United States Patent
Mueller et al.

(10) Patent No.: US 9,492,440 B2
(45) Date of Patent: *Nov. 15, 2016

(54) BICYCLIC AMIDES FOR ENHANCING GLUTAMATERGIC SYNAPTIC RESPONSES

(75) Inventors: Rudolf Mueller, Foothill Ranch, CA (US); Leslie Street, Laguna Niguel, CA (US)

(73) Assignee: RESPIRERX PHARMACEUTICALS INC, Glen Rock, NJ (US)

( * ) Notice: Subject to any disclaimer, the term of this patent is extended or adjusted under 35 U.S.C. 154(b) by 440 days.

This patent is subject to a terminal disclaimer.

(21) Appl. No.: 13/557,681

(22) Filed: Jul. 25, 2012

(65) Prior Publication Data

US 2013/0190351 A1   Jul. 25, 2013

Related U.S. Application Data

(62) Division of application No. 12/733,073, filed as application No. PCT/US2008/009508 on Aug. 8, 2008, now Pat. No. 8,263,591.

(60) Provisional application No. 60/964,362, filed on Aug. 10, 2007.

(51) Int. Cl.

| | | |
|---|---|---|
| A61K 31/535 | (2006.01) |
| C07D 498/02 | (2006.01) |
| C07D 265/00 | (2006.01) |
| A61K 31/519 | (2006.01) |
| A61K 31/53 | (2006.01) |
| C07D 209/52 | (2006.01) |
| A61K 31/46 | (2006.01) |
| C07D 451/04 | (2006.01) |
| C07D 451/06 | (2006.01) |
| C07D 453/06 | (2006.01) |
| C07D 471/08 | (2006.01) |
| C07D 491/08 | (2006.01) |
| A61K 31/4245 | (2006.01) |
| A61K 31/439 | (2006.01) |
| A61K 45/06 | (2006.01) |
| C07D 451/02 | (2006.01) |
| C07D 487/08 | (2006.01) |

(52) U.S. Cl.
CPC ........... *A61K 31/46* (2013.01); *A61K 31/4245* (2013.01); *A61K 31/439* (2013.01); *A61K 31/519* (2013.01); *A61K 31/53* (2013.01); *A61K 45/06* (2013.01); *C07D 209/52* (2013.01); *C07D 451/02* (2013.01); *C07D 451/04* (2013.01); *C07D 451/06* (2013.01); *C07D 453/06* (2013.01); *C07D 471/08* (2013.01); *C07D 487/08* (2013.01); *C07D 491/08* (2013.01)

(58) Field of Classification Search
None
See application file for complete search history.

(56) References Cited

U.S. PATENT DOCUMENTS

| | | |
|---|---|---|
| 3,723,436 A | 3/1973 | Hollstein et al. |
| 4,797,482 A | 1/1989 | Constansa et al. |
| 5,650,409 A | 7/1997 | Rogers et al. |
| 5,736,543 A | 4/1998 | Rogers et al. |
| 5,747,492 A | 5/1998 | Lynch et al. |
| 5,783,587 A | 7/1998 | Rogers et al. |
| 5,962,447 A | 10/1999 | Rogers et al. |
| 6,030,968 A | 2/2000 | Gall et al. |
| 6,303,542 B1 | 10/2001 | Li et al. |
| 2002/0055508 A1 | 5/2002 | Rogers et al. |
| 2002/0099050 A1 | 7/2002 | Lynch et al. |
| 2003/0153752 A1 | 8/2003 | Hirst et al. |
| 2005/0026952 A1 | 2/2005 | Mathias |
| 2005/0148603 A1 | 7/2005 | Jimenez et al. |
| 2010/0041647 A1 | 2/2010 | Mueller et al. |
| 2010/0120764 A1 | 5/2010 | Street et al. |

FOREIGN PATENT DOCUMENTS

| | | |
|---|---|---|
| DE | 2012094 | 9/1971 |
| WO | WO9402475 | 2/1994 |
| WO | 9736907 | 10/1997 |
| WO | 9835950 A1 | 8/1998 |
| WO | 9921422 A1 | 5/1999 |
| WO | 9933469 | 7/1999 |
| WO | WO9942456 | 8/1999 |
| WO | 03099299 A1 | 12/2003 |
| WO | 2008025148 A1 | 3/2008 |

(Continued)

OTHER PUBLICATIONS

Monaghan et al., in Brain Research 324:160-164 (1984).
Arai and Lynch, Brain Research 598:173-184 (1992).
Granger et al., Synapse 15:326-329 (1993).
Staubli et al., PNAS 91:777-781 (1994).
Arai et al., Brain Res. 638:343-346 (1994).
Staubli et al., PNAS 91:11158-11162 (1994).
Shors et al., Neurosci. Let. 186:153-156 (1995).
Larson et al., J. Neurosci. 15:8023-8030 (1995).
Granger et al., Synapse 22:332-337 (1996).
Arai et al., JPET 278:627-638 (1996).
Lynch et al., Internat. Clin. Psychopharm. 11: 13-19 (1996).
Lynch et al., Exp. Neurology 145:89-92 (1997).
Ingvar et al., Exp. Neurology 146:553-559 (1997).
Hampson, et al., J. Neurosci. 18:2748-2763 (1998).
Porrino et al., PLoS Biol 3(9):1-14 (2006).

(Continued)

*Primary Examiner* — Samantha Shterengarts
(74) *Attorney, Agent, or Firm* — Henry D. Coleman; R. Neil Sudol

(57) ABSTRACT

This invention relates to bicyclic amide compounds, pharmaceutical compositions and methods for use in the prevention and treatment of a variety of conditions and/or disease states including cerebral insufficiency, through the enhancement of receptor functioning in synapses in brain networks responsible for basic and higher order behaviors as defined herein. These brain networks, which are involved in regulation of breathing, and cognitive abilities related to memory impairment, such as is observed in a variety of dementias, in imbalances in neuronal activity between different brain regions, as is suggested in disorders such as Parkinson's disease, schizophrenia, respiratory depression, sleep apneas, attention deficit hyperactivity disorder and affective or mood disorders, and in other disorders wherein a deficiency in neurotrophic factors is implicated, as well as other disorders as described herein.

18 Claims, No Drawings

(56) References Cited

FOREIGN PATENT DOCUMENTS

| WO | 2008085505 A1 | 7/2008 |
|----|---------------|--------|
| WO | 2008085506 A1 | 7/2008 |
| WO | 2008143963 A1 | 11/2008 |
| WO | 2009023126 A2 | 2/2009 |
| WO | 2009038752 A2 | 3/2009 |

OTHER PUBLICATIONS del Cerro and Lynch, Neuroscience 49: 1-6 (1992).
Whitlock et al., Science 313:1093-1097 (2006).
Pastalkova, et al., Science 313:1141-1144 (2006).
Rex, et al., J. Neurophysiol. 96:677-685 (2006).
Lauterborn, et al., J. Neurosci. 20:8-21 (2000).
Lauterborn, et al., JPET 307:297-305 (2003).
Mackowiak, et al., Neuropharmacology 43:1-10 (2002).
O'Neill, et al., Eur. J. Pharmacol. 486:163-174 (2004).
Kent, et al., Mol. Psychiatry 10:939-943 (2005).
Riikonen, et al., J. Child Neurol. 18:693-697 (2003).
Chang, et al., Neuron 49:341-348 (2006).
Ito et al., J. Physiol. 424:533-543 (1990).
Staubli et al., Psychobiology 18:377-381 (1990).
Xiao et al., Hippocampus 1:373-380 (1991).
Guenzi and Zanetti, J. Chromatogr. 530:397-406 (1990).
Himori, et al., Pharmacology Biochemistry and Behavior 47:219-225 (1994).
Pizzi et al., J. Neurochem. 61:683-689 (1993).
Nakamura and Shirane, Eur. J. Pharmacol. 380: 81-89 (1999).
Spignoli and Pepeu, Pharmacol. Biochem. Behav. 27:491-495 (1987).
Hall and Von Voigtlander, Neuropharmacology 26:1573-1579(1987).
Kessler et al., Brain Res. 560: 337-341 (1991).
Staubli et al., Hippocampus 2: 4958 (1992).
Sirvio et al., Neuroscience 74: 1025-1035 (1996).
Chapter 7, Neuroscience, edited by Dale Purves, Sinauer Associates, Inc., Sunderland, MA 1997.
Diagnostic and Statistical Manual of Mental Disorders, Fourth Edition (DSM IV), pp. 317-391.
Diagnostic and Statistical Manual of Mental Disorders, Fourth Edition (DSM IV) Sections 293.81, 293.82, 295.10, 295.20, 295.30, 295.40, 295.60, 295.70, 295.90, 297.1, 297.3, 298.8.
http://www.chemdrug.com/database/10_3_gbflimrcjilwki.html.
Gouaux et al.,Structure and function of AMPA receptors. J. Physiol. 2003, 554, 249-253.
Gueyrard et al. A new and rapid access to homochiral 2,3-dihydro-oxazolo[2,3-b]quinazolin-5-ones, Tetrahedron: Assymmetry 2001, 12, 337-340.
Murray et al. LY503430, a novel AMPA receptor potentiator with functional, neuroprotective and neurotrophic effects in rodent models of Parkinson's disease. J. Pharmacol. Exp. Ther. 2003, 306, 752-762.
Russell, Increased AMPA Receptor Function in Slices Containing the Prefrontal Cortex of Spontaneously Hypertensive Rats. Metabolic Brain Disease, 2001, 16, 143-149.
Pontarelli. New drug that enhances glutamate transmission in brain being evaluated for fragile X. printed Apr. 10, 2008 from Http://www.innovations-report.com/html/reports/medicine_health/report-12386.html.
Ren. Ampakines alleviate respiratory depression in rats. American Journal of Respiratory and Critical Care Medicine 2006, 174, 1384-1391.
Database Registry [online] Jun. 25, 2006, XP002591764 retrieved from STN accession No. RN889315-82-6.
Database Registry [online] Chemical Abstracts Serevice, Columbus, Ohio, US; Dec. 18, 2007, XP002592000. retrieved from STN accession No. RN958588-26-6.
Morissette et al. Advanced Drug Delivery Reviews 2004, 56, 275-300.
Vippagunta et al., abstract, Vippagunta, Sudha R. "Crystalline Solids" Advanced Drug Delivery Reviews 48(2001): 3-26.

BICYCLIC AMIDES FOR ENHANCING GLUTAMATERGIC SYNAPTIC RESPONSES

RELATED APPLICATIONS

This application is a divisional of and claims the benefit of priority of U.S. National Stage patent application Ser. No. 12/733,073 filed Jul. 19, 2010 entitled "BICYCLIC AMIDES FOR ENHANCING GLUTAMATERGIC SYNAPTIC RESPONSES", now U.S. Pat. No. 8,263,591, which claims the benefit of priority of Internatioanl Patent Application No. PCT/US2008/009508 filed 8 Aug. 2008 which claims the benefit of priority of provisional patent application Ser. No. US60/964,362, filed Aug. 10, 2007 of identical title, the entire contents of which all three applicaiotns are incorporated by reference herein.

FIELD OF THE INVENTION

This invention relates to compounds, pharmaceutical compositions and methods for use in the prevention and treatment of cerebral insufficiency, including enhancement of receptor functioning in synapses in brain networks responsible for various behaviors. These brain networks are involved in basic functions such as breathing, to more complex functions such as memory and cognition. Imbalances in neuronal activities between different brain regions may lead to a number of disorders, including psychiatric and neurological disorders, including memory impairment, Parkinson's disease, schizophrenia, attention deficit and affective or mood disorders, respiratory depression and in disorders wherein a deficiency in neurotrophic factors is implicated. In a particular aspect, the invention relates to compounds useful for treatment of such conditions, and methods of using these compounds for such treatment.

BACKGROUND OF THE INVENTION

The release of glutamate at synapses at many sites in mammalian forebrain stimulates two classes of postsynaptic ionotropic glutamate receptors. These classes are usually referred to as AMPA and N-methyl-D-aspartic acid (NMDA) receptors. AMPA receptors mediate a voltage independent fast excitatory post-synaptic current (the fast EPSC), whereas NMDA receptors generate a voltage-dependent, slow excitatory current. Studies carried out in slices of hippocampus or cortex, indicate that the AMPA receptor mediated fast EPSC is generally the dominant component by far at most glutamatergic synapses, and activation of AMPA receptors is usually a prerequisite for NMDA receptors activation.

AMPA receptors are expressed throughout the central nervous system. These receptors are found in high concentrations in the superficial layers of neocortex, in each of the major synaptic zones of hippocampus, and in the striatal complex, as reported by Monaghan et al., in Brain Research 324:160-164 (1984). Studies in animals and humans indicate that these structures organize complex perceptual-motor processes and provide the substrates for higher-order behaviors. Thus, AMPA receptors mediate transmission in those brain networks responsible for a host of cognitive activities. In addition, AMPA receptors are expressed in brain regions that regulate the inspiratory drive responsible for control of breathing (Paarmann et al, Journal of Neurochemistry, 74: 1335-1345 (2000).

For the reasons set forth above, drugs that modulate and thereby enhance the functioning of AMPA receptors could have significant benefits for intellectual performance as well as reversal of respiratory depression induced by pharmacological agents such as opioids and opiates, or other means. Such drugs should also facilitate memory encoding. Experimental studies, such as those reported by Arai and Lynch, Brain Research 598:173-184 (1992), indicate that increasing the size of AMPA receptor-mediated synaptic response(s) enhances the induction of long-term potentiation (LTP). LTP is a stable increase in the strength of synaptic contacts that follows repetitive physiological activity of a type known to occur in the brain during learning.

Compounds that enhance the functioning of the AMPA subtype of glutamate receptors facilitate the induction of LTP and the acquisition of learned tasks as measured by a number of paradigms. See, for example, Granger et al., Synapse 15:326-329 (1993); Staubli et al., PNAS 91:777-781 (1994); Arai et al., Brain Res. 638:343-346 (1994); Staubli et al., PNAS 91:11158-11162 (1994); Shors et al., Neurosci. Let. 186:153-156 (1995); Larson et al., J. Neurosci. 15:8023-8030 (1995); Granger et al., Synapse 22:332-337 (1996); Arai et al., JPET 278:627-638 (1996); Lynch et al., Internat. Clin. Psychopharm. 11:13-19 (1996); Lynch et al., Exp. Neurology 145:89-92 (1997); Ingvar et al., Exp. Neurology 146:553-559 (1997); Hampson, et al., J. Neurosci. 18:2748-2763 (1998); Porrino et al., PLoS Biol 3(9): 1-14 (2006) and Lynch and Rogers, U.S. Pat. No. 5,747,492. There is a considerable body of evidence showing that LTP is the substrate of memory. For example, compounds that block LTP interfere with memory formation in animals, and certain drugs that disrupt learning in humans antagonize the stabilization of LTP, as reported by del Cerro and Lynch, Neuroscience 49: 1-6 (1992). Learning a simple task induces LTP in hippocampus that occludes LTP generated by high frequency stimulation (Whitlock et al., Science 313:1093-1097 (2006)) and a mechanism that maintains LTP sustains spatial memory (Pastalkova, et al., Science 313:1141-1144 (2006)). Of significant importance to the field of learning is the finding that in vivo treatments with a positive AMPA-type glutamate receptor modulator restores stabilization of basal dendritic LTP in middle-aged animals (Rex, et al., J. Neurophysiol. 96:677-685 (2006)).

Drugs that enhance the functioning of the AMPA receptor can effectively reverse opioid- and barbiturate-induced respiratory depression without reversing the analgesic response (Ren et al, American Journal of Respiratory and Critical Care Medicine, 174: 1384-1391 (2006). Therefore these drugs may be useful in preventing or reversing opioid-induced respiratory depression and for alleviating other forms of respiratory depression including sedative use and sleep apnea. Excitatory synaptic transmission provides a major pathway by which neurotrophic factors are increased within specific brain regions. As such, potentiation of AMPA receptor function by modulators has been found to increase levels of neurotrophins, particularly brain derived neurotrophic factor, or BDNF. See, for example, Lauterborn, et al., J. Neurosci. 20:8-21 (2000); Gall, et al., U.S. Pat. No. 6,030,968; Lauterborn, et al., JPET 307:297-305 (2003); and Mackowiak, et al., Neuropharmacology 43:1-10 (2002). Other studies have linked BDNF levels to a number of neurological disorders, such as Parkinson's disease, Attention Deficit Hyperactivity Disorder (ADHD), autism, Fragile-X Syndrome, and Rett Syndrome (RTT). See, for example, O'Neill, et al., Eur. J. Pharmacol. 486:163-174 (2004); Kent, et al., Mol. Psychiatry. 10:939-943 (2005); Riikonen, et al., J. Child Neurol. 18:693-697 (2003) and Chang, et al., Neuron 49:341-348 (2006). Thus, AMPA receptor potentiators may be useful for the treatment of these, as well as other, neurological diseases that are the result of a glutamatergic imbalance or a deficit in neurotrophic factors.

A prototype for a compound that selectively facilitates the AMPA receptor has been described by Ito et al., *J. Physiol.* 424:533-543 (1990). These authors found that the nootropic drug aniracetam (N-anisoyl-2-pyrrolidinone) increases currents mediated by brain AMPA receptors expressed in *Xenopus oocytes* without affecting responses by γ-aminobutyric acid (GABA), kainic acid (KA), or NMDA receptors. Infusion of aniracetam into slices of hippocampus was also shown to substantially increase the size of fast synaptic potentials without altering resting membrane properties. It has since been confirmed that aniracetam enhances synaptic responses at several sites in hippocampus, and that it has no effect on NMDA-receptor mediated potentials (Staubli et al., *Psychobiology* 18:377-381 (1990) and Xiao et al., *Hippocampus* 1:373-380 (1991)).

Aniracetam has been found to have an extremely rapid onset and washout, and can be applied repeatedly with no apparent lasting effects, which are desirable features for behaviorally-relevant drugs. Aniracetam does present several disadvantages, however. The peripheral administration of aniracetam is not likely to influence brain receptors. The drug works only at high concentrations (approx. 1000 μM), and about 80% of the drug is converted to anisoyl-GABA following peripheral administration in humans (Guenzi and Zanetti, *J. Chromatogr.* 530:397-406 (1990)). The metabolite, anisoyl-GABA, has been found to have less activity than aniracetam. In addition to these issues, aniracetam has putative effects on a plethora of other neurotransmitter and enzymatic targets in the brain, which makes uncertain the mechanism of any claimed therapeutic drug effect. See, for example, Himori, et al., *Pharmacology Biochemistry and Behavior* 47:219-225 (1994); Pizzi et al., *J. Neurochem.* 61:683-689 (1993); Nakamura and Shirane, *Eur. J. Pharmacol.* 380: 81-89 (1999); Spignoli and Pepeu, *Pharmacol. Biochem. Behav.* 27:491-495 (1987); Hall and Von Voigtlander, *Neuropharmacology* 26:1573-1579 (1987); and Yoshimoto et al., *J. Pharmacobiodyn.* 10:730-735 (1987).

A class of AMPA receptor-enhancing compounds that does not display the low potency and inherent instability characteristic of aniracetam has been described (Lynch and Rogers, U.S. Pat. No. 5,747,492). These compounds, termed "Ampakines"[R], can be substituted benzamides which include, for example, 6-(piperidin-1-ylcarbonyl)quinoxaline (CX516; Ampalex[R]). Typically, they are chemically more stable than aniracetam and show improved bio-availability. CX516 is active in animal tests used to detect efficacious drugs for the treatment of memory disorders, schizophrenia, and depression. In three separate clinical trials, CX516 showed evidence for efficacy in improving various forms of human memory (Lynch et al., *Internat. Clin. Psychopharm.* 11:13-19 (1996); Lynch et al., *Exp. Neurology* 145:89-92 (1997); Ingvar et al., *Exp. Neurology* 146:553-559 (1997)).

Another class of Ampakines, benzoxazines, has been discovered to have very high activity in in vitro and in vivo models for assessing the probability of producing cognition enhancement (Rogers and Lynch; U.S. Pat. No. 5,736,543). The substituted benzoxazines are rigid benzamide analogues with different receptor modulating properties from the flexible benzamide, CX516.

Certain substituted 2.1.3 benzoxadiazole compounds have been found to be significantly and surprisingly more potent in animal models of attention deficit hyperactivity disorder (ADHD), schizophrenia and cognition than previously disclosed compounds in US 2002/0055508 and US 2002/0099050. This new and novel class of bicyclic amides (A), described in greater detail herein, display significant activity for enhancing AMPA mediated glutamateric synaptic responses.

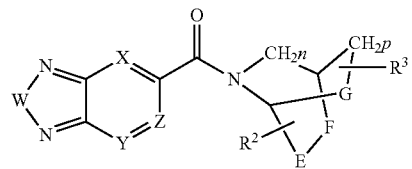

SUMMARY OF THE INVENTION

The present invention therefore, includes, in one aspect, a compound as shown by structure A and other structures and described in Section H of the Detailed Description, which follows. Administration of compounds of this class has been found to enhance AMPA mediated glutamatergic synaptic responses and significantly improve the behavior of rodents in the d-amphetamine stimulated locomotion assay. This behavioral assay has proven useful in assessing the efficacy of neuroleptic drugs for the treatment of schizophrenia and ADHD. The compounds are significantly and surprisingly more potent than previously described compounds in increasing glutamatergic synaptic responses in vivo. This activity translates into pharmaceutical compounds and corresponding methods of use, including treatment methods, which utilize significantly lower concentrations of the present compounds compared to prior art compositions. In addition, compounds within the present invention demonstrate improved pharmacokinetic properties compared with previously described compounds and have good oral bio-availability.

The ability of the compounds of the invention to increase AMPA receptor-mediated responses makes the compounds useful for a variety of purposes. These include facilitating the learning of behaviors dependent upon glutamate receptors, treating conditions in which AMPA receptors, or synapses utilizing these receptors, are reduced in numbers or efficiency, and enhancing excitatory synaptic activity in order to restore an imbalance between brain sub-regions or increase the levels of neurotrophic factors.

In another aspect, the invention includes a method for the treatment of a mammalian subject suffering from a hypoglutamatergic condition, or from a deficiency in the number or strength of excitatory synapses, or in the number of AMPA receptors, such that memory or other cognitive functions are impaired. Such conditions may also cause a cortical/striatal imbalance, leading to schizophrenia or schizophreniform behavior.

In another aspect, the invention includes a method for reducing or inhibiting respiratory depression in a subject having respiratory depression, comprising administering to the subject an amount of a compound of the invention, the amount being sufficient to reduce or inhibit respiratory depression. In one embodiment of the invention, the subject is a human. In another embodiment, the subject is a mammal. Also claimed is a method for reducing or inhibiting respiratory depression comprising administering to the subject an amount of a compound of the invention in combination with an opioid analgesic; examples of such opiates include but are not limited to, alfentanil and fentanyl.

In another aspect, the invention includes a method for reducing or inhibiting breathing-related sleep disorders or sleep apnea in a subject having sleep apnea, comprising administering to the subject an amount of a compound of the invention, the amount being sufficient to reduce or inhibit the breathing related sleep disorder.

According to the methods, such a subject is treated with an effective amount of a compound as shown by structure I, and described in Section II of the Detailed Description, following, in a pharmaceutically acceptable carrier. These and other objects and features of the invention will become more fully apparent when the following detailed description of the invention is read in conjunction with the accompanying drawings.

DETAILED DESCRIPTION OF THE INVENTION

I. Definitions

The terms below have the following meanings unless indicated otherwise. Other terms that are used to describe the present invention have the same definitions as those terms are generally used by those skilled in the art.

The term "alkyl" is used herein to refer to a fully saturated monovalent radical containing carbon and hydrogen, and which may be a straight chain, branched or cyclic. Examples of alkyl groups are methyl, ethyl, n-butyl, n-heptyl, isopropyl, 2-methylpropyl.

The term "cycloalkyl" is used herein to refer to a fully saturated monovalent radical containing up to 8 carbons and hydrogen in a ring. Examples of cycloalkyl groups are cyclopropyl, cyclobutyl, cyclopentyl, cyclohexyl and cycloheptyl.

The term "bicycloalkyl" is used herein to refer to a fully saturated monovalent radical containing up to 10 carbons and hydrogen in a bicyclic ring. Examples of bicycloalkyl groups are bicyclo[2.2.2]octyl, bicyclo[2.2.1]heptyl and bicyclo[2.2.3]nonyl and bicylo[3.2.1]octyl.

The term "azabicycloalkyl" is used herein to refer to a fully saturated monovalent radical containing up to 10 carbons and hydrogen and 1 nitrogen atom in a bicyclic ring. Examples of azabicycloalkyl groups a include 1-azabicyclo[2.2.2]octyl, 2-azabicyclo[2.2.2]octyl, 1-azabicyclo[2.2.1]heptyl, 2-azabicyclo[2.2.1]heptyl and 1-azabicylo[3.2.1]octyl.

The term "alkenyl" is used herein to refer to a monovalent radical containing carbon and hydrogen that contains one or two sites of un-saturation, and which may be a straight chain, branched or cyclic. Examples of alkenyl groups are ethenyl, n-butenyl, n-heptenyl, isopropenyl, cyclopentenyl, cyclopentenylethyl and cyclohexenyl. "Alkynyl" refers to a monovalent radical containing carbon and hydrogen as described above which contains at least one triple bond.

The term "substituted alkyl" refers to alkyl as just described including one or more functional groups such as lower alkyl containing 1-6 carbon atoms, aryl, substituted aryl, acyl, halogen (i.e., alkyl halos, e.g., $CF_3$), amido, thioamido cyano, nitro, alkynyl, azido, hydroxy, alkoxy, alkoxyalkyl, amino, alkyl and dialkyl-amino, acylamino, acyloxy, aryloxy, aryloxyalkyl, carboxyalkyl, carboxamido, thio, thioethers, both saturated and unsaturated cyclic hydrocarbons, heterocycles and the like.

The term "aryl" refers to a substituted or unsubstituted monovalent aromatic radical having a single ring (e.g., phenyl) or multiple condensed rings (e.g., naphthyl). Other examples include heterocyclic aromatic ring groups having one or more nitrogen, oxygen, or sulfur atoms in the ring, such as oxazolyl, isoxazolyl, pyrazolyl, thiazolyl, thiadiazolyl, tetrazolyl, pyridazinyl, pyrimidyl, benzofuryl, benzothienyl, benzimidazolyl, benzoxazolyl, benzothiazolyl, quinolyl, isoquinolyl, imidazolyl, furyl, pyrrolyl, pyridyl, thienyl and indolyl.

The term "substituted" as used in the term "substituted aryl, substituted aromatic, substituted heteroaryl, or substituted heteroaromatic" herein signifies that one or more substituents may be present, said substituents being selected from atoms and groups, which when present do not prevent the compound from functioning as a potentiator of AMPA receptor function. Examples of substituents that may be present in a substituted aromatic or heteroaromatic group include, but are not limited to, groups such as ($C_1$-$C_7$) alkyl, ($C_1$-$C_7$) acyl, aryl, heteroaryl, substituted aryl and heteroaryl, halogen, cyano, nitro, amido (optionally substituted with one or two $C_1$-$C_7$ alkyl groups), thioamido (optionally substituted with one or two $C_1$-$C_7$ alkyl groups), azido, alkynyl, ($C_1$-$C_7$) alkylhalos (e.g., $CF_3$), hydroxy, ($C_1$-$C_7$) alkoxy, ($C_2$-$C_8$) alkoxyalkyl, amino, ($C_1$-$C_7$) alkyl and dialkyl amino, ($C_1$-$C_7$) acylamino, ($C_1$-$C_7$) acyloxy, aryloxy, ($C_1$-$C_7$) aryloxyalkyl, ($C_1$-$C_7$) carboxyalkyl, carboxamido, thio, ($C_1$-$C_7$) thioethers, both saturated and unsaturated ($C_3$-$C_8$) cyclic hydrocarbons, ($C_3$-$C_8$) heterocycles and the like. It is noted that each of the substituents disclosed herein may themselves be substituted.

"Heterocycle" or "heterocyclic" refers to a carbocylic ring wherein one or more carbon atoms have been replaced with one or more heteroatoms such as nitrogen, oxygen or sulfur. Examples of heterocycles include, but are not limited to, piperidine, pyrrolidine, morpholine, thiomorpholine, piperazine, tetrahydrofuran, tetrahydropyran, 2-pyrrolidinone, δ-valerolactam, δ-valerolactone and 2-ketopiperazine.

The term "substituted heterocycle" refers to a heterocycle as just described which contains or is substituted with one or more functional groups (as otherwise described herein) such as lower alkyl, acyl, aryl, cyano, halogen, amido, thioamido, azido, hydroxy, alkoxy, alkoxyalkyl, amino, alkyl and dialkyl-amino, acylamino, acyloxy, aryloxy, aryloxyalkyl, carboxyalkyl, carboxamido, thio, thioethers, both saturated and unsaturated cyclic hydrocarbons, heterocycles and the like, as otherwise described herein.

The term "compound" is used herein to refer to any specific chemical compound disclosed herein. Within its use in context, the term generally refers to a single stable compound, but in certain instances may also refer to stereoisomers and/or optical isomers (including enantiopure compounds, enantiomerically enriched compounds and racemic mixtures) of disclosed compounds.

The term "effective amount" refers to the amount of a selected compound of formula I that is used within the context of its intended use to effect an intended result, for example, to enhance glutamatergic synaptic response by increasing AMPA receptor activity. The precise amount used will vary depending upon the particular compound selected and its intended use, the age and weight of the subject, route of administration, and so forth, but may be easily determined by routine experimentation. In the case of the treatment of a condition or disease state, an effective amount is that amount which is used to effectively treat the particular condition or disease state.

The term "pharmaceutically acceptable carrier" refers to a carrier or excipient which is not unacceptably toxic to the subject to which it is administered. Pharmaceutically acceptable excipients are described at length by E. W. Martin, in "Remington's Pharmaceutical Sciences."

A "pharmaceutically acceptable salt" of an amine compound, such as those contemplated in the current invention, is an ammonium salt having as counter ion an inorganic anion such as chloride, bromide, iodide, sulfate, sulfite, nitrate, nitrite, phosphate, and the like, or an organic anion such as acetate, malonate, pyruvate, propionate, fumarate, cinnamate, tosylate, and the like.

The term "patient" or "subject" is used throughout the specification to describe an animal, generally a mammalian animal, including a human, to whom treatment or use with the compounds or compositions according to the present invention is provided. For treatment or use with/or of those conditions or disease states which are specific for a specific animal (especially, for example, a human subject or patient), the term patient or subject refers to that particular animal.

The term "sensory motor problems" is used to describe a problem which arises in a patient or subject from the inability to integrate external information derived from the five known senses in such a way as to direct appropriate physical responses involving movement and action.

The term "cognitive task" or "cognitive function" is used to describe an endeavor or process by a patient or subject that involves thought or knowing. The diverse functions of the association cortices of the parietal, temporal and frontal lobes, which account for approximately 75% of all human brain tissue, are responsible for much of the information processing that goes on between sensory input and motor output. The diverse functions of the association cortices are often referred to as cognition, which literally means the process by which we come to know the world. Selectively attending to a particular stimulus, recognizing and identifying these relevant stimulus features and planning and experiencing the response are some of the processes or abilities mediated by the human brain which are related to cognition.

The term "brain network" is used to describe different anatomical regions of the brain that communicate with one another via the synaptic activity of neuronal cells.

The term "AMPA receptor" refers to an aggregate of proteins found in some membranes, which allows positive ions to cross the membrane in response to the binding of glutamate or AMPA (DL-α-amino-3-hydroxy-5-methyl-4-isoxazolepropionic acid), but not NMDA.

The term "excitatory synapse" is used to describe a cell-cell junction at which release of a chemical messenger by one cell causes depolarization of the external membrane of the other cell. An excitatory synapse describes a postsynaptic neuron which has a reversal potential that is more positive than the threshold potential and consequently, in such a synapse, a neurotransmitter increases the probability that an excitatory post synaptic potential will result (a neuron will fire producing an action potential). Reversal potentials and threshold potentials determine postsynaptic excitation and inhibition. If the reversal potential for a post synaptic potential ("PSP") is more positive than the action potential threshold, the effect of a transmitter is excitatory and produces an excitatory post synaptic potential ("EPSP") and the firing of an action potential by the neuron. If the reversal potential for a post synaptic potential is more negative than the action potential threshold, the transmitter is inhibitory and may generate inhibitory post synaptic potentials (IPSP), thus reducing the likelihood that a synapse will fire an action potential. The general rule for postsynaptic action is: if the reversal potential is more positive than threshold, excitation results; inhibition occurs if the reversal potential is more negative than threshold. See, for example, Chapter 7, *NEUROSCIENCE*, edited by Dale Purves, Sinauer Associates, Inc., Sunderland, Mass. 1997.

The term "motor task" is used to describe an endeavor taken by a patient or subject that involves movement or action.

The term "perceptual task" is used to describe an act by a patient or subject of devoting attention to sensory inputs.

The term "synaptic response" is used to describe biophysical reactions in one cell as a consequence of the release of chemical messengers by another cell with which it is in close contact.

The term "hypoglutamatergic condition" is used to describe a state or condition in which transmission mediated by glutamate (or related excitatory amino acids) is reduced to below normal levels. Transmission consists of the release of glutamate, binding to post synaptic receptors, and the opening of channels integral to those receptors. The end point of the hypoglutamatergic condition is reduced excitatory post synaptic current. It can arise from any of the three above noted phases of transmission. Conditions or disease states which are considered hypoglutamatergic conditions and which can be treated using the compounds, compositions and methods according to the present invention include, for example, loss of memory, dementia, depression, attention disorders, sexual dysfunction, movement disorders, including Parkinson's disease, schizophrenia or schizophreniform behavior, memory and learning disorders, including those disorders which result from aging, trauma, stroke and neurodegenerative disorders, such as those associated with drug-induced states, neurotoxic agents, Alzheimer's disease and aging, respiratory depression and sleep apnea. These conditions are readily recognized and diagnosed by those of ordinary skill in the art.

The term "cortico-striatal imbalance" is used to describe a state in which the balance of neuronal activities in the interconnected cortex and underlying striatal complex deviates from that normally found. 'Activity' can be assessed by electrical recording or molecular biological techniques. Imbalance can be established by applying these measures to the two structures or by functional (behavioral or physiological) criteria.

The term "affective disorder" or "mood disorder" describes the condition when sadness or elation is overly intense and continues beyond the expected impact of a stressful life event, or arises endogenously. As used herein, the term "effective disorder" embraces all types of mood disorders as described in, for example, *Diagnostic and Statistical Manual of Mental Disorders*, Fourth Edition (DSM IV), pages 317-391.

The term "schizophrenia" is used to describe a condition which is a common type of psychosis, characterized by a disorder in the thinking processes, such as delusions and hallucinations, and extensive withdrawal of the individual's interest from other people and the outside world, and the investment of it in his or her own. Schizophrenia is now considered a group of mental disorders rather than a single entity, and distinction is made between reactive and process schizophrenias. As used herein, the term schizophrenia or "schizophreniform" embraces all types of schizophrenia, including ambulatory schizophrenia, catatonic schizophrenia, hebephrenic schizophrenia, latent schizophrenia, process schizophrenia, pseudoneurotic schizophrenia, reactive schizophrenia, simple schizophrenia, and related psychotic disorders which are similar to schizophrenia, but which are not necessarily diagnosed as schizophrenia per se. Schizophrenia and other psychotic disorders may be diagnosed using guidelines established in, for example, *Diagnostic and Statistical Manual of Mental Disorders*, Fourth Edition (DSM IV) Sections 293.81, 293.82, 295.10, 295.20, 295.30, 295.40, 295.60, 295.70, 295.90, 297.1, 297.3, 298.8.

The term "brain function" is used to describe the combined tasks of perceiving, integrating, filtering and responding to external stimuli and internal motivational processes.

The term "impaired" is used to describe a function working at a level that is less than normal. Impaired functions can be significantly impacted such that a function is barely being carried out, is virtually non-existent or is working in a fashion that is significantly less than normal. Impaired functions may also be sub-optimal. The impairment of function will vary in severity from patient to patient and the condition to be treated.

The term "respiratory depression" as used herein refers to a variety of conditions characterized by reduced respiratory frequency and inspiratory drive to cranial and spinal motor neurons. Specifically, respiratory depression refers to conditions where the medullary neural network associated with respiratory rhythm generating activity does not respond to accumulating levels of $PCO_2$ (or decreasing levels of $PO_2$) in the blood and subsequently under stimulates motorneurons controlling lung musculature.

The term "sleep apnea" as used herein refers to breathing-related sleep disorders of which there are two types: central and obstructive. Central Sleep Apnea is defined as a neurological condition causing cessation of all respiratory effort during sleep, usually with decreases in blood oxygen saturation, if the brainstem center controlling breathing shuts down there's no respiratory effort and no breathing. The person is aroused from sleep by an automatic breathing reflex, so may end up getting very little sleep at all. Obstructive sleep apnea is characterized by repetitive pauses in breathing during sleep due to the obstruction and/or collapse of the upper airway and followed by an awakening to breathe. Respiratory effort continues during the episodes of apnea.

The term "pro-drug" as used herein refers to a metabolically labile derivative that is pharmacologically inactive in the parent form but that is rapidly metabolized in human or animal plasma to a pharmacologically active form. Examples of pro-drugs as used herein include but in no way are limited to ester derivatives of hydroxyl containing moieties, such esters include but are not limited to those formed from substituted or un-substituted natural or un-natural amino acids.

II. Compounds of the Present Invention

The present invention is directed to compounds having the property of enhancing AMPA receptor function. These include compounds having the structure A, below:

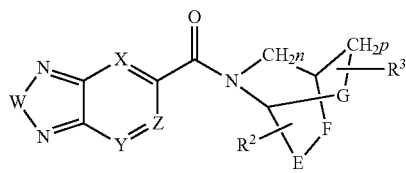

wherein:

W is oxygen, sulfur or CH=CH;

X, Y and Z are independently selected from the group consisting of —N, or —CR, wherein:

R is H, —Br, —Cl, —F, —CN, —$NO_2$, —$OR^1$, —$SR^1$, —$NR^1_2$, —$C_1$-$C_6$ branched or un-branched alkyl, which may be un-substituted or substituted, wherein:

$R^1$ is H, —$C_1$-$C_6$ branched or un-branched alkyl which, may be un-substituted or substituted, n=0-5 (such that from 0 to 5 methylene groups are present)
m=0-5 (such that from 0 to 5 methylene groups are present)
p=0-5 (such that from 0 to 5 methylene groups are present)

$R^2$ and $R^3$ are each independently selected from H, a halogen (preferably F), —CN, —$NO_2$, —$OR^1$, —$SR^1$, —$NR^1_2$, $CF_3$, OH, C=O, a —$C_1$-$C_6$ branched or un-branched alkyl, which may be un-substituted or substituted, a —$C_2$-$C_6$ branched or un-branched alkenyl, which may be un-substituted or substituted, a —$C_2$-$C_6$ branched or un-branched alkynyl, which may be un-substituted or substituted, a —$C_3$-$C_7$ cycloalkyl which may be un-substituted or substituted, an aryl which may be un-substituted or substituted, a heterocycle which may be un-substituted or substituted, a carboxyalkyl which may be un-substituted or substituted, a carboxyaryl which may be un-substituted or substituted, a carboxyheteroaryl which may be un-substituted or substituted, a sulfonylalkyl which may be un-substituted or substituted, a sulfonylaryl which may be un-substituted or substituted or a sulfonylheteroaryl which may be un-substituted or substituted, E and F are each independently selected from $CH_2$m, $CR^2R^3$, A, $CH_2$A, $CR^2$=$CR^3$ or are absent, with the proviso that E and F are not both absent;

G is $CR^2R^3$, A, $CH_2$A, $CR^2$=$CR^3$, $CH_2$C=O, $CH_2CR^2R^3$, or absent,

A is O, S, SO, $SO_2$, C=O or $CR^2R^3$;

or a pharmaceutically acceptable salt, solvate, or polymorph thereof.

The present invention is directed, in another aspect, to compounds having the property of enhancing AMPA receptor function. These include compounds having the structure I, below:

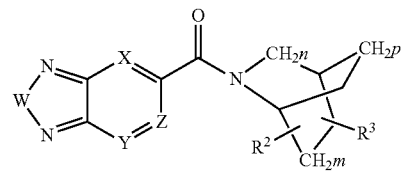

wherein:

W is oxygen, sulfur or CH=CH;

X, Y and Z are independently selected from the group consisting of —N, or —CR, wherein:

R is H, —Br, —Cl, —F, —CN, —$NO_2$, —$OR^1$, —$SR^1$, —$NR^1_2$, —$C_1$-$C_6$ branched or un-branched alkyl, which may be un-substituted or substituted, wherein:

$R^1$ is H, —$C_1$-$C_6$ branched or un-branched alkyl which, may be un-substituted or substituted, n=0-5 (such that from 0 to 5 methylene groups are present)
m=0-5 (such that from 0 to 5 methylene groups are present)
p=0-5 (such that from 0 to 5 methylene groups are present)

$R^2$ and $R^3$ are independently selected from H, a halogen (preferably F), —CN, —$NO_2$, —$OR^1$, —$SR^1$, —$NR^1_2$, $CF_3$, OH, C=O, a —$C_1$-$C_6$ branched or un-branched alkyl, which may be un-substituted or substituted, a —$C_2$-$C_6$ branched or un-branched alkenyl, which may be un-substituted or substituted, a —$C_2$-$C_6$ branched or un-branched alkynyl, which may be un-substituted or substituted, a —$C_3$-$C_7$ cycloalkyl which may be un-substituted or substituted, an aryl which may be un-substituted or substituted, a heterocycle which may be un-substituted or substituted, a carboxyalkyl which may be un-substituted or substituted, a carboxyaryl which may be un-substituted or substituted, a carboxyheteroaryl which may be un-substituted or substituted, a sulfonylalkyl which may be un-substituted or substituted, a sulfonylaryl which may be un-substituted or substituted or a sulfonylheteroaryl which may be un-substituted or substituted, or a pharmaceutically acceptable salt, solvate, or polymorph thereof.

The azabicyclic ring may also be an unsaturated azabicyclic ring as represented by structure II:

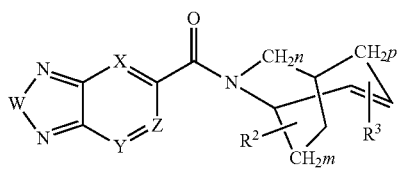

II wherein:
W, X, Y and Z are as defined for structure I, above
n=0-5 (such that from 0 to 5 methylene groups are present)
m=0-5 (such that from 0 to 5 methylene groups are present)
p=0-4 (such that from 0 to 4 methylene groups are present)
and $R^2$ and $R^3$ are as defined for structure I, or a pharmaceutically acceptable salt, solvate, or polymorph thereof.

The azabicyclic ring may also be represented by structure III:

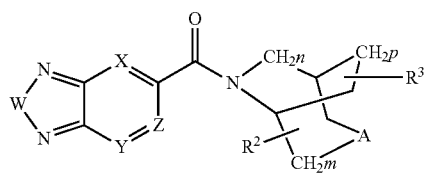

III wherein:
W, X, Y and Z are as defined for structure I, above
A is O, S, SO, $SO_2$, C=O or $CR^2R^3$;
n=0-5 (such that from 0 to 5 methylene groups are present)
m=1-5 (such that from 1 to 5 methylene groups are present)
p=0-5 (such that from 0 to 5 methylene groups are present)
and $R^2$ and $R^3$ are as defined for structure I, or a pharmaceutically acceptable salt, solvate, or polymorph thereof.

In a further aspect of the present invention, the azabicyclic ring includes compounds of structure IV:

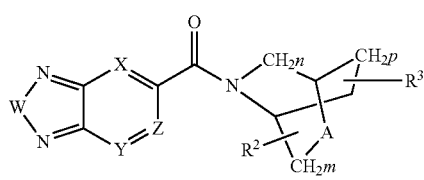

IV wherein:
W, X, Y and Z are as defined for structure I, above
A is O, S, SO, $SO_2$, C=O or $CR^2R^3$;
n=1-5 (such that from 1 to 5 methylene groups are present)
m=1-5 (such that from 1 to 5 methylene groups are present)
p=0-5 (such that from 0 to 5 methylene groups are present)
and $R^2$ and $R^3$ are as defined for structure I, or a pharmaceutically acceptable salt, solvate, or polymorph thereof.

In a further aspect, the present invention provides compounds of Formulas A and I-IV selected from:

8-Azabicyclo[3.2.1]oct-8-yl([2,1,3]-benzoxadiazol-5-yl)methanone 8-([2,1,3]-Benzoxadiazol-5-ylcarbonyl)-8-azabicyclo[3.2.1]octan-3-one

[2,1,3]-Benzoxadiazol-5-yl(3,3-difluoro-8-azabicyclo[3.2.1]oct-8-yl)-methanone

[2,1,3]-Benzoxadiazol-5-yl(3-fluoro-8-azabicyclo[3.2.1]oct-2-en-8-yl)methanone endo-[2,1,3]-Benzoxadiazol-5-yl(3-hydroxy-8-azabicyclo[3.2.1]oct-8-yl)methanone exo-[2,1,3]-Benzoxadiazol-5-yl(3-hydroxy-8-azabicyclo[3.2.1]oct-8-yl)methanone 2-Azabicyclo[2.2.1]hept-2-yl([2,1,3]-benzoxadiazol-5-yl)methanone 1-Azabicyclo[2.2.1]hept-1-yl([2,1,3]-benzoxadiazol-5-yl)methanone 2-Azabicyclo[2.2.2]oct-2-yl([2,1,3]-benzoxadiazol-5-yl)methanone

[2,1,3]-Benzoxadiazol-5-yl(2-oxa-5azabicyclo[2.2.1]hept-5-yl)methanone

2-Azabicyclo[2.2.1]hept-5-en-2-yl([2,1,3]-benzoxadiazol-5-yl)-methanone

[2,1,3]-Benzoxadiazol-5-yl(5,6-dichloro-2-azabicyclo[2.2.1]hept-2-yl)-methanone

R-2-Azabicyclo[2.2.1]hept-5-en-2-yl([2,1,3]-benzoxadiazol-5-yl)-methanone

S-2-Azabicyclo[2.2.1]hept-5-en-2-yl([2,1,3]-benzoxadiazol-5-yl)methanone

III. Synthesis

The synthesis of the compounds of the invention, are preferably carried out by the following Scheme. Alternative syntheses by analogy relying on methodology that exists in the art also may be used. Each compound may be made using the described synthesis by following the proposed chemistry as presented herein or by making minor modifications in the synthetic chemistry relying on well known methods available in the art. The approach to synthesis is rather facile and may be readily modified within the scope of the present teachings. Acid chloride 4 is synthesized starting with 4-amino-3-nitrobenzoic acid 1 by firstly oxidizing using bleach to give intermediate 2 and then reducing with triethyl phosphite ($P(OEt)_3$) to give benzofurazan carboxylic acid 3. The carboxylic acid 3 was transformed to the acid chloride 4 by refluxing with thionyl chloride and a catalytic amount of DMF in toluene. The carboxylic acid 3 can be transformed into bicyclic amides 5 by reaction with aminobicycles using standard coupling conditions like CDI, EDCI, HBTU in a suitable solvent. Alternatively, acid chloride 4 can be transformed into bicyclic amides 5 under standard coupling conditions with bicyclic amines in the presence of a base for example triethylamine or aqueous sodium hydroxide, among others in a suitable solvent, for example dichloromethane. The benzothiadiazole amides 6 are prepared from the commercially available benzothiadiazole acid chloride under standard coupling conditions in the presence of a base for example triethylamine or aqueous sodium hydroxide in a suitable solvent for example dichloromethane. Quinoxaline-6-carboxylic acid chloride is prepared by condensation of commercially available 3,4-diaminobenzoic acid with glyoxal followed by refluxing with thionyl chloride and a catalytic amount of DMF in toluene using standard procedures. Reaction of quinoxaline-6-carboxylic acid chloride with bicyclic amines gave the desired quinoxaline bicyclic amides (7). The alternative azabicycles as represented by structures II-IV are made in a similar fashion using the appropriate azabicycle to couple with the carboxyxlic acid chloride 4.

In another aspect, the invention provides a method for reducing or inhibiting respiratory depression in a subject having such a condition, comprising administering to the subject an amount of a compound of the invention, the amount being sufficient to reduce or inhibit respiratory depression. In a further aspect of the invention, a method is provided for reducing or inhibiting respiratory depression comprising administering to the subject an amount of a compound of the invention in combination with an opiate; examples of such opiates include but are not limited to, alfentanil and fentanyl.

In a further aspect, the invention provides a method for reducing or inhibiting breathing-related sleep disorders or sleep apnea in a subject having sleep apnea, comprising administering to the subject an amount of a compound of the invention, the amount being sufficient to reduce or inhibit the breathing related sleep disorder.

In the present invention, the method of treatment comprises administering to the subject in need of treatment, in a pharmaceutically acceptable carrier, an effective amount of a compound having the Formula A below:

Scheme

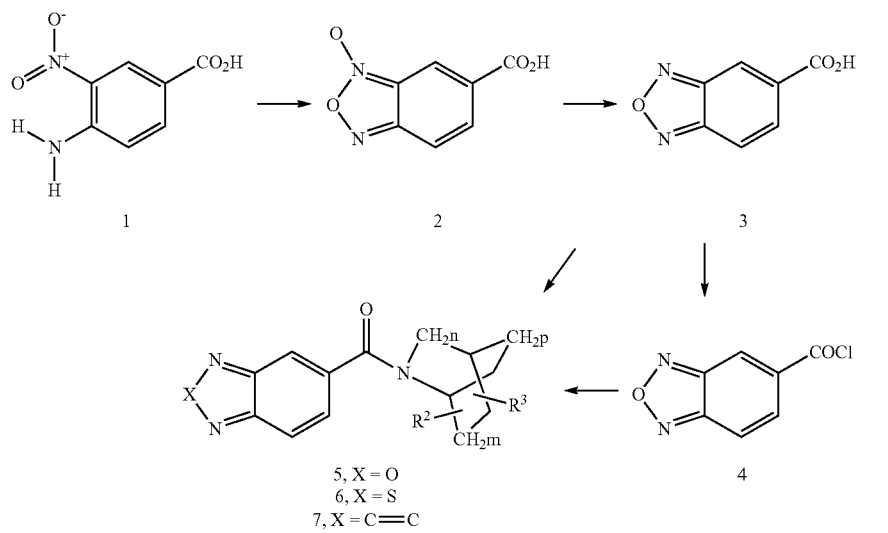

5, X = O
6, X = S
7, X = C═C

IV. Method of Treatment

According to one aspect of the invention, a method is provided for treating a mammalian subject suffering from a hypoglutamatergic condition, or from deficiencies in the number or strength of excitatory synapses or in the number of AMPA receptors. In such a subject, memory or other cognitive functions may be impaired, or cortical/striatal imbalance may occur, leading to loss of memory, dementia, depression, attention disorders, sexual dysfunction, movement disorders, schizophrenia or schizophreniform behavior. Memory disorders and learning disorders, which are treatable according to the present invention include those disorders that result from aging, trauma, stroke and neurodegenerative disorders. Examples of neurodegenerative disorders include, but are not limited to, those associated with drug-induced states, neurotoxic agents, Alzheimer's disease, and aging.

These conditions are readily recognized and diagnosed by those of ordinary skill in the art and treated by administering to the patient an effective amount of one or more compounds according to the present invention.

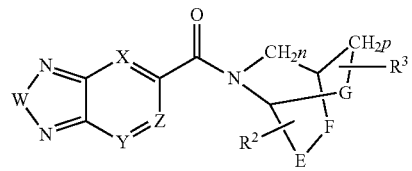

A wherein:

W is oxygen, sulfur or CH═CH;

X, Y and Z are independently selected from the group consisting of —N, or —CR, wherein:

R is H, —Br, —Cl, —F, —CN, —NO$_2$, —OR$^1$, —SR$^1$, —NR$^1_2$, —C$_1$-C$_6$ branched or un-branched alkyl, which may be un-substituted or substituted, wherein:

R$^1$ is H, —C$_1$-C$_6$ branched or un-branched alkyl which, may be un-substituted or substituted, n=0-5 (such that from 0 to 5 methylene groups are present)
m=0-5 (such that from 0 to 5 methylene groups are present)
p=0-5 (such that from 0 to 5 methylene groups are present)
$R^2$ and $R^3$ are each independently selected from H, a halogen (preferably F), —CN, —$NO_2$, —$OR^1$, —$SR^1$, —$NR^1_2$, $CF_3$, OH, C=O, a —$C_1$-$C_6$ branched or un-branched alkyl, which may be un-substituted or substituted, a —$C_2$-$C_6$ branched or un-branched alkenyl, which may be un-substituted or substituted, a —$C_2$-$C_6$ branched or un-branched alkynyl, which may be un-substituted or substituted, a —$C_3$-$C_7$ cycloalkyl which may be un-substituted or substituted, an aryl which may be un-substituted or substituted, a heterocycle which may be un-substituted or substituted, a carboxyalkyl which may be un-substituted or substituted, a carboxyaryl which may be un-substituted or substituted, a carboxyheteroaryl which may be un-substituted or substituted, a sulfonylalkyl which may be un-substituted or substituted, a sulfonylaryl which may be un-substituted or substituted or a sulfonylheteroaryl which may be un-substituted or substituted, E and F are each independently selected from $CH_2m$, $CR^2R^3$, A, $CH_2A$, $CR^2$=$CR^3$ or are absent, with the proviso that E and F are not both absent;

G is $CR^2R^3$, A, $CH_2A$, $CR^2$=$CR^3$, $CH_2C$=O, $CH_2CR^2R^3$, or absent,

A is O, S, SO, $SO_2$, C=O or $CR^2R^3$;

or a pharmaceutically acceptable salt, solvate, or polymorph thereof.

In a further aspect of the present invention, the method of treatment comprises administering to the subject in need of treatment, in a pharmaceutically acceptable carrier, an effective amount of a compound having the Formula I below:

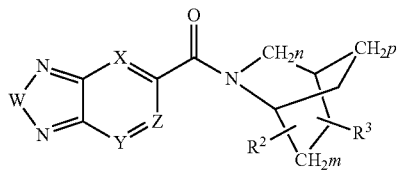

I wherein:
W is oxygen, sulfur or CH=CH;
X, Y and Z are independently selected from the group consisting of —N, or —CR,
wherein:
R is H, —Br, —Cl, —F, —CN, —$NO_2$, —$OR^1$, —$SR^1$, —$NR^1_2$, —$C_1$-$C_6$ branched or un-branched alkyl, which may be un-substituted or substituted,
wherein:
$R^1$ is H, —$C_1$-$C_6$ branched or un-branched alkyl which may be un-substituted or substituted,
n=0-5 (such that from 0 to 5 methylene groups are present)
m=0-5 (such that from 0 to 5 methylene groups are present)
p=0-5 (such that from 0 to 5 methylene groups are present)
$R^2$ and $R^3$ are independently selected from H, a halogen (preferably F), —CN, —$NO_2$, —$OR^1$, —$SR^1$, —$NR^1_2$, $CF_3$, OH, C=O, a —$C_1$-$C_6$ branched or un-branched alkyl, which may be un-substituted or substituted, a —$C_2$-$C_6$ branched or un-branched alkenyl, which may be un—substituted or substituted, a —$C_2$-$C_6$ branched or un-branched alkynyl, which may be un-substituted or substituted, a —$C_3$-$C_7$ cycloalkyl which may be un-substituted or substituted, an aryl which may be un-substituted or substituted, a heterocycle which may be un-substituted or substituted, a carboxyalkyl which may be un-substituted or substituted, a carboxyaryl which may be un-substituted or substituted, a carboxyheteroaryl which may be un-substituted or substituted, a sulfonylalkyl which may be un-substituted or substituted, a sulfonylaryl which may be un-substituted or substituted or a sulfonylheteroaryl which may be un-substituted or substituted, or a pharmaceutically acceptable salt, solvate, or polymorph thereof.

In a further method aspect of the invention azabicyclic compounds represented by structure II are preferred to be used in the method aspect:

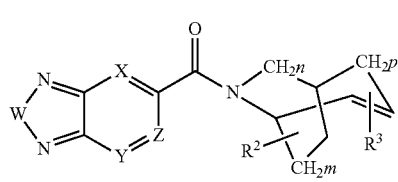

II wherein:
W, X, Y and Z are as defined for structure I
n=0-5
m=0-5
p=0-4
and $R^2$ and $R^3$ are as defined for structure I, or a pharmaceutically acceptable salt, solvate, or polymorph thereof.

In yet a further method aspect of the invention, preferred embodiments include compounds represented by structure III:

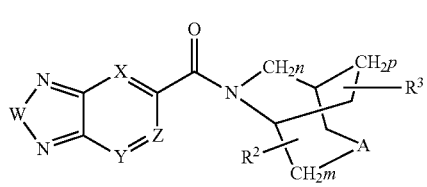

III wherein:
W, X, Y and Z are as defined for structure I
A is O, S, SO, $SO_2$, C=O or $CR^2R^3$;
n=0-5
m=1-5
p=0-5
and $R^2$ and $R^3$ are as defined for structure I, or a pharmaceutically acceptable salt, solvate, or polymorph thereof.

In yet a further method aspect of the invention, preferred embodiments include compounds represented by structure IV:

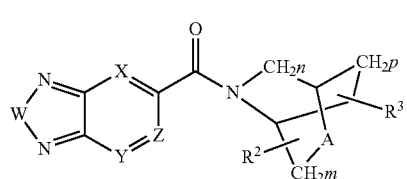

IV wherein:
W, X, Y and Z are as defined for structure I
A is O, S, SO, $SO_2$, C=O or $CR^2R^3$;

n=1-5
m=1-5
p=0-5
and $R^2$ and $R^3$ are as defined for structure I, or a pharmaceutically acceptable salt, solvate, or polymorph thereof.

Compounds according to the present invention exhibit enhanced bioavailability in most instances due, at least in part, to enhanced pharmacokinetics exhibited by the present compounds. Accordingly, the present compounds may be favorably formulated into pharmaceutical compositions in a variety of dosage forms, and in particular, oral dosage forms.

As noted above, treatment of a subject according to the method of the invention is useful for enhancing AMPA receptor activity, and thus may be used to facilitate the learning of behaviors dependent upon AMPA receptors, and to treat conditions, such as memory impairment, in which AMPA receptors, or synapses utilizing these receptors, are reduced in numbers or efficiency. The method is also useful for enhancing excitatory synaptic activity in order to restore an imbalance between brain sub-regions, which may manifest itself in schizophrenia or schizophreniform behavior, or other behavior as described above. The compounds administered in accordance with the method have been found to be more effective than previously described compounds in enhancing AMPA receptor activity, as shown in the in vivo tests described below.

V. Biological Activity

A. Enhancement of AMPA Receptor Function In Vivo.

Synaptic responses mediated by AMPA receptors are increased according to the method of the invention, using the compounds described herein.

The electrophysiological effects of the invention compounds were tested in vivo in anesthetized animals according to the following procedures. Animals are maintained under anesthesia by phenobarbital administered using a Hamilton syringe pump. Stimulating and recording electrodes are inserted into the perforant path and dentate gyrus of the hippocampus, respectively. Once electrodes are implanted, a stable baseline of evoked responses are elicited using single monophasic pulses (100 µs pulse duration) delivered at 3/min to the stimulating electrode. Field EPSPs are monitored until a stable baseline is achieved (about 20-30 min), after which a solution of test compound is injected intraperitoneally and evoked field potentials are recorded. Evoked potentials were recorded for approximately 2 h following drug administration or until the amplitude of the field EPSP returns to baseline. In the latter instance, it is common that an iv administration is also carried out with an appropriate dose of the same test compound. Invention compounds were assayed in the in vivo electrophysiology assay described above and data for representative test compounds is shown in column 1 in Table 1. Compounds of the invention are significantly more active in increasing the amplitude of the field EPSP in the rat dentate gyrus following i.p. dosing than CX516 (1-(quinoxalin-6-ylcarbonyl)piperidine; U.S. Pat. No. 5,773,434, US2002/0055508) which gave a 9% increase in amplitude of the field EPSP at 50 mg/kg i.p.

TABLE 1

| Compound Example Number | [1]In vivo Electrophysiology | [2]Inhibition of d-Amphetamine Stimulated Locomotion |
| --- | --- | --- |
| 1 | 22% | 69% |
| 2 | 16% | 40% |
| 3 | 8% | NT |
| 4 | 25% | NT |
| 7 | 20%[3] | NT |

[1]% increase in the amplitude of the field EPSP in the dentate gyrus of rat @ 10 mpk i.p.
[2]% Inhibition of d-amphetamine stimulated locomotion in mice @ 18 mpk i.p.
[3]Dosed i.v.
NT = Not tested B. Behavioral Testing: Inhibition of d-Amphetamine Stimulated Locomotion The ability of the invention compounds to inhibit d-Amphetamine stimulated locomotor activity was assayed according to the following procedure. Male CD1 mice, 25-30 gm body weight, were brought into the experimental room and allowed at least 30 min of acclimation. Each mouse was placed into the testing enclosure with an infrared beam array that automatically monitors the animal's activity. Mice were habituated in the testing enclosure for 20 min, and then returned to their home cage. Mice were dosed intraperitoneally with test compound in appropriate vehicle 5 minutes before d-Amphetamine injection (2 mpk). Ten minutes after d-Amphetamine injection, mice were tested for locomotor activity for a total of 15 minutes. The data was computer collected and expressed as "arbitrary movement units." All data were analyzed by comparing the groups treated with the test compound to the vehicle control group. The data for test compounds is shown in Table 1, column 2. The data shown is the % inhibition of hyperactivity induced by acute administration of 2 mg/kg d-amphetamine in mice. The compounds tested produced a statistically significant inhibition of d-amphetamine stimulated locomotion.

VI. Administration, Dosages, and Formulation

As noted above, the compounds and method of the invention increase glutamatergic synaptic responses mediated by AMPA receptors, and are useful for the treatment of hypoglutamatergic conditions. They are also useful for treatment of conditions such as impairment of memory or other cognitive functions, brought on by a deficiency in the number or strength of excitatory synapses, or in the number of AMPA receptors. They may also be used in the treatment of schizophrenia or schizophreniform behavior resulting from a cortical/striatal imbalance, and in facilitation of learning of behaviors dependent upon AMPA receptors.

In subjects treated with the present compounds, pharmaceutical compositions and methods memory or other cognitive functions may be impaired or cortical/striatal imbalance may occur, leading to loss of memory, dementia, depression, attention disorders, sexual dysfunction, movement disorders, schizophrenia or schizophreniform behavior. Memory disorders and learning disorders, which are treatable according to the present invention, include those disorders that result from aging, trauma, stroke and neurodegenerative disorders. Examples of neurodegenerative disorders include, but are not limited to, those associated with drug-induced states, neurotoxic agents, Alzheimer's disease, and aging. These conditions are readily recognized and diagnosed by those of ordinary skill in the art and treated by administering to the patient an effective amount of one or more compounds according to the present invention.

Generally, dosages and routes of administration of the compound will be determined according to the size and condition of the subject, according to standard pharmaceutical practices. Dose levels employed can vary widely, and can readily be determined by those of skill in the art. Typically, amounts in the milligram up to gram quantities are employed. The composition may be administered to a subject by various routes, e.g. orally, transdermally, perineurally or parenterally, that is, by intravenous, subcutaneous, intraperitoneal, or intramuscular injection, among others, including buccal, rectal and transdermal administration. Subjects contemplated for treatment according to the method of the invention include humans, companion animals, laboratory animals, and the like.

Formulations containing the compounds according to the present invention may take the form of solid, semi-solid, lyophilized powder, or liquid dosage forms, such as, for example, tablets, capsules, powders, sustained-release formulations, solutions, suspensions, emulsions, suppositories, creams, ointments, lotions, aerosols, patches or the like, preferably in unit dosage forms suitable for simple administration of precise dosages.

Pharmaceutical compositions according to the present invention comprise an effective amount of one or more compounds according to the present invention and typically include a conventional pharmaceutical carrier or excipient and may additionally include other medicinal agents, carriers, adjuvants, additives and the like. Preferably, the composition will be about 0.5 to 75% by weight or more of a compound or compounds of the invention, with the remainder consisting essentially of suitable pharmaceutical excipients. For oral administration, such excipients include pharmaceutical grades of mannitol, lactose, starch, magnesium stearate, sodium saccharine, talcum, cellulose, glucose, gelatin, sucrose, magnesium carbonate, and the like. If desired, the composition may also contain minor amounts of non-toxic auxiliary substances such as wetting agents, emulsifying agents, or buffers.

Liquid compositions can be prepared by dissolving or dispersing the compounds (about 0.5% to about 20% by weight or more), and optional pharmaceutical adjuvants, in a carrier, such as, for example, aqueous saline, aqueous dextrose, glycerol, or ethanol, to form a solution or suspension. For use in oral liquid preparation, the composition may be prepared as a solution, suspension, emulsion, or syrup, being supplied either in liquid form or a dried form suitable for hydration in water or normal saline.

When the composition is employed in the form of solid preparations for oral administration, the preparations may be tablets, granules, powders, capsules or the like. In a tablet formulation, the composition is typically formulated with additives, e.g. an excipient such as a saccharide or cellulose preparation, a binder such as starch paste or methyl cellulose, a filler, a disintegrator, and other additives typically used in the manufacture of medical preparations.

An injectable composition for parenteral administration will typically contain the compound in a suitable i.v. solution, such as sterile physiological salt solution. The composition may also be formulated as a suspension in a lipid or phospholipid, in a liposomal suspension, or in an aqueous emulsion.

Methods for preparing such dosage forms are known or will be apparent to those skilled in the art; for example, see Remington's Pharmaceutical Sciences (17th Ed., Mack Pub. Co., 1985).

The composition to be administered will contain a quantity of the selected compound in a pharmaceutically effective amount for effecting increased AMPA receptor currents in a subject.

The following examples illustrate but are not intended in any way to limit the invention. Unless otherwise stated, all temperatures are given in degrees Celsius. Unless otherwise stated, all NMR spectra are $^1$H NMR spectra and were obtained in deuterochloroform or deuterated DMSO as solvent using tetramethylsilane as an internal standard. All names of Example compounds conform to IUPAC nomenclature as provided by the computer software ChemSketch by ACD Labs.

I. Chemical Methods

Intermediate 1

2,1,3-Benzoxadiazole-5-carboxylic acid

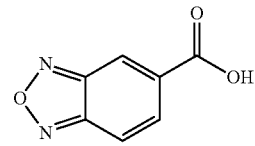 [SMILES: O=C(O)c1ccc2nonc2c1]

In a 3 L reactor fitted with mechanical stirring, reflux condenser, thermometer and nitrogen inlet, KOH (72.46 g) was dissolved in ethanol (250 ml) and water (250 ml). 4-Amino-3-nitrobenzoic acid (100 g) was added and the orange suspension was heated to 65-70° C. within 30 minutes. The resulting suspension was stirred at the same temperature for 45 minutes and cooled to 0° C.±5° C. within 30 minutes. A commercially available (13% w/w) solution of sodium hypochlorite (448.93 g) was added drop wise within 1.5 hours at 0° C.±5° C. The reaction mixture was stirred at the same temperature for 2 hours and controlled by TLC (CHCl$_3$ 100/acetone 2/acetic acid 1). Water (350 ml) was added within 15 minutes at 0° C.±5° C. to give a fine yellow suspension. The reaction mixture was then acidified with a 6N HCl solution (239 ml) until 0.5<pH<1 was reached. NaCl (58.44 g) was added and the resulting suspension was stirred at 0° C.±5° C. for 1.5 hours under nitrogen. The solid was collected by filtration, washed with 3×400 ml water and dried (40° C., 30 mbars, 12 hours) to yield 83.6 g (88.8% yield) of 2,1,3-benzoxadiazole-5-carboxylic acid N-oxide.

In a 2 L reactor fitted with mechanical stirring, thermometer, addition funnel, reflux condenser and nitrogen inlet, 2,1,3-benzoxadiazole-5-carboxylic acid N-oxide (80 g) was dissolved in absolute ethanol (800 ml). To this solution triethyl phosphite (114.05 g) was added within 10 minutes at 70° C.±2° C. The resulting mixture was heated to reflux (76-78° C.) and maintained for 2 hours. TLC monitoring (CHCl$_3$ 100/acetone 2/acetic acid 1) showed complete reaction. The solvent was removed under vacuum (30 mbars, 40° C.) which yielded a black oil (180 g). Water (400 ml) was added and the mixture was extracted with ethyl acetate (400 and 160 ml). The organic phase was extracted with 850 ml water containing NaOH (9.5<pH<10). The aqueous phase was separated and extracted with ethyl acetate (3×240 ml). The aqueous phase was acidified (78 ml 6 N HCl) to 1<pH<2 at 5° C.±2° C. which resulted in the crystallization of the yellow product, which was filtered off and dried (40° C., 30 mbars, 12 hours) to yield 65.56 g (90% yield) 2,1,3-benzoxadiazole-5-carboxylic acid: mp=160-161° C.,

$^1$H NMR (300 MHz, DMSO) δ 13.8 (s, 1H); 8.57 (s, 1H); 8.56 (d, 1H, J=0.6 Hz); 7.87 ppm (d, 1H, J=0.6 Hz).

Intermediate 2

2,1,3-Benzoxadiazole-5-carbonylchloride

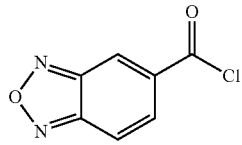 [SMILES: O=C(Cl)c1ccc2nonc2c1]

In a 500 ml reactor fitted with mechanical stirring, thermometer, addition funnel, reflux condenser and nitrogen inlet, 2,1,3-benzoxadiazole-5-carboxylic acid (28 g) was suspended in toluene (245 ml). To this suspension was added thionyl chloride (39.4 g) and DMF (0.35 ml). The resulting mixture was heated to reflux and maintained for 3 hours. A short pass column was installed and toluene was distilled (atmospheric pressure, 124 ml) off to remove excess reagent. After cooling the remaining toluene was distilled off, which resulted in a thick oil. This oil was distilled (90° C., 2 mm Hg) to remove impurities and the product crystallized on standing (79.8% yield), mp: 55-58° C.

EXAMPLE 1

8-Azabicyclo[3.2.1]oct-8-yl([2,1,3]-benzoxadiazol-5-yl)methanone

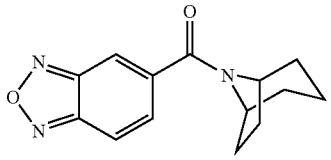 [SMILES: O=C(c1ccc2nonc2c1)N1C2CCCC1CC2]

To a solution of tropane (2.5 g, 20 mmol) in toluene (80 ml) was slowly added [2,2,2]-trichloroethyl chloroformate (20 ml, 94.4 mmol) and $Na_2CO_3$ (1.5 g, 14 mmol). The mixture was heated to 110° C. overnight. The solution was cooled to room temperature, ethyl acetate (150 ml), water (100 ml) and $H_2SO_4$ (→ pH 2) were added. The organic phase was dried over sodium sulfate, and concentrated under vacuum to yield 9.3 g colorless oil. The preceding product (3.3 g) was dissolved in THF (50 ml) and methanol (50 ml), and freshly prepared Zn/Cu (15 g) was added followed by formic acid (5 ml). The mixture was stirred at room temperature for 20 minutes before filtering the solids and evaporating the solvent until ~10 ml remained. Concentrated sodium hydroxide solution was added until pH 10 was reached and the mixture extracted with chloroform (100 ml) and the organic phase dried over sodium sulfate. Triethylamine (2 ml) was added followed by a solution of [2,1,3]-benzoxadiazole-5-carbonylchloride (0.5 g, 2.73 mmol) in chloroform (20 ml), slowly. After stirring the mixture for 20 minutes, water (100 ml) and $H_2SO_4$ (→ pH2) were added and the aqueous phase extracted with chloroform (100 ml), dried over magnesium sulfate, and concentrated under vacuum to give an oil. The material was purified by silica gel chromatography eluting with hexane/ethyl acetate (3:2), to give after crystallization from dichloromethane/MTBE 133 mg of a white solid: mp=128-130° C., LC-MS, $MH^+$=258; $^1$H NMR (300 MHz, $CDCl_3$) δ 7.92 (s, 1H); 7.90 (d, 1H, J=6.3 Hz); 7.52 (d, 1H, J=6.3 Hz); 4.84 (s, 1H); 4.06 (s, 1H); 2.06-1.50 ppm (m, 10H).

EXAMPLE 2

8-([2,1,3]-Benzoxadiazol-5-ylcarbonyl)-8-azabicyclo[3.2.1]octan-3-one

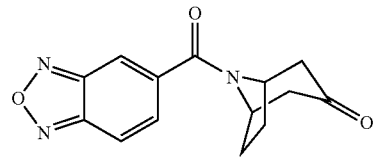 [SMILES: O=C1CC2CCC(C1)N2C(=O)c1ccc2nonc2c1]

To a solution of tropinone (10 g, 71.8 mmol) in toluene (120 ml) was slowly added [2,2,2]-trichloroethyl chloroformate (40 ml, 189 mmol) and sodium carbonate (4.0 g, 37.7 mmol). The mixture was heated to 110° C. for 42 hours, the solvent evaporated, water (100 ml) and $H_2SO_4$ (→ pH 2) added and the mixture extracted with ethyl acetate (3×100 ml). The organic phase was dried over sodium sulfate, concentrated under vacuum and the residue purified by silica gel chromatography eluting with hexane/ethyl acetate (4:1) to give an oil (12.9 g) which solidified on standing. To a solution of this product (2.5 g) in THF (40 ml) and methanol (40 ml) was added freshly prepared Zn/Cu (12 g) and the mixture stirred at room temperature for 1 h. Triethylamine (3 ml) was added, the solids filtered off and washed with methanol (10 ml), and the solvent evaporated. The residue was dissolved in chloroform (80 ml), and triethylamine (3 ml) was added followed by slow addition of a solution of [2,1,3]-benzoxadiazole-5-carbonylchloride (1.5 g, 8.2 mmol) in chloroform (20 ml). After stirring the mixture for 1 h, water (100 ml) and $H_2SO_4$ (→ pH2) were added and the aqueous phase extracted with chloroform (100 ml). The combined organics were washed with $NaHCO_3$ solution (100 ml), dried over sodium sulfate, and concentrated under vacuum. The residue was purified by silica gel chromatography eluting with hexane/ethyl acetate (1:1) to give a solid that was crystallized from dichloromethane/MTBE (1.04 g): mp=164-166° C., LC-MS, $MH^+$=272; $^1$H NMR (300 MHz, $CDCl_3$) δ 8.02 (s, 1H); 7.97 (d, 1H, J=9 Hz); 7.57 (d, 1H, J=9 Hz); 5.09 (sb, 1H); 4.44 (sb, 1H); 3.05-1.80 ppm (m, 8H).

EXAMPLE 3 and EXAMPLE 4

[2,1,3]-Benzoxadiazol-5-yl(3,3-difluoro-8-azabicyclo[3.2.1]oct-8-yl)methanone and [2,1,3]-benzoxadiazol-5-yl(3-fluoro-8-azabicyclo[3.2.1]oct-2-en-8-yl)methanone

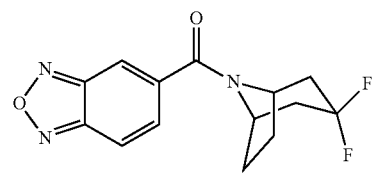

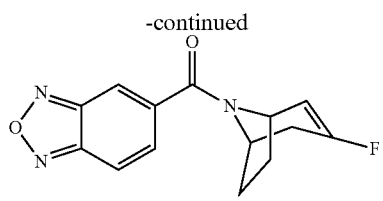

To a solution of 8-([2,1,3]-benzoxadiazol-5-ylcarbonyl)-8-azabicyclo[3.2.1]octan-3-one (0.67 g, 2.45 mmol) in dichloromethane (25 ml) was slowly added diethylaminosulfur trifluoride, "DAST" (5 g). The mixture was stirred at room temperature for 3 days and then slowly poured into a mixture of NaHCO$_3$ solution (100 ml) and chloroform (100 ml). The aqueous phase was extracted with chloroform (100 ml) and the combined organics were dried over sodium sulfate, concentrated under vacuum and the residue purified by silica gel chromatography eluting with hexane/ethyl acetate (65:35), to give [2,1,3]-benzoxadiazol-5-yl(3,3-difluoro-8-azabicyclo[3.2.1]oct-8-yl)methanone (0.37 g) after crystallization from dichoromethane/MTBE and as the less polar of 2 products: mp=165-166° C., LC-MS, MH$^+$=294; $^1$H NMR (300 MHz, CDCl$_3$) δ 7.96-7.93 (m, 2H); 7.54-7.50 (m, 1H); 5.00 (sb, 1H); 4.26 (sb, 1H); 2.60-2.05 ppm (m, 8H).

A second more polar product was identified as [2,1,3]-benzoxadiazol-5-yl(3-fluoro-8-azabicyclo[3.2.1]oct-2-en-8-yl)methanone and was crystallized from dichoromethane/MTBE (0.06 g): mp=133-137° C., LC-MS, MH$^+$=274; $^1$H NMR (300 MHz, CDCl$_3$) δ 8.00-7.87 (m, 2H); 7.53 (d, 1H, J=8.7 Hz); 5.70-5.45 (m, 1H); 5.05 (sb, 1H); 4.31 (sb, 1H); 3.23-1.45 ppm (m, 6H).

EXAMPLE 5 endo-[2,1,3]-Benzoxadiazol-5-yl(3-hydroxy-8-azabicyclo[3.2.1]oct-8-yl)methanone

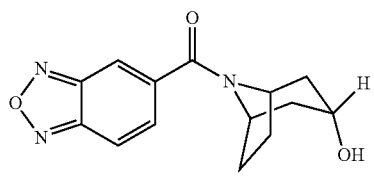 [SMILES: O=C(c1ccc2nonc2c1)N1C2CCC1CC(O)C2]

To a solution of tropine (4.0 g, 28.3 mmol) in toluene (50 ml) was slowly added [2,2,2]-trichloroethyl chloroformate (16 ml, 75.5 mmol) and Na$_2$CO$_3$ (4.0 g, 37.7 mmol). The mixture was heated to 110° C. for 42 hours, the toluene removed under vacuum, water (150 ml) and H$_2$SO$_4$ (→ pH 2) were added, and the mixture extracted with ethyl acetate (2×100 ml). The combined organics were dried over sodium sulfate, concentrated under vacuum and the residue chromatographed on silica gel using hexane/ethyl acetate (70:30) → (40:60) to give a white solid (6.0 g). To a solution of the preceding product (2.5 g, 8.26 mmol) in THF (50 ml) and methanol (50 ml), was added freshly prepared Zn/Cu (15 g) and the mixture stirred at room temperature for 18 h. The solids were filtered off, the solvent evaporated and to the residue, dissolved in DMF (60 ml), were added DMAP (0.98 g, 8 mmol), HOBT (0.54 g, 4 mmol), triethylamine (2 ml), [2,1,3]-benzoxadiazole-5-carboxylic acid (1.31 g, 8 mmol) and EDCI (3 g, 15.6 mmol) and the mixture stirred at room temperature for 2 days. The DMF was evaporated and water (100 ml) and H$_2$SO$_4$ (→ pH2) were added. The mixture was extracted with chloroform (2×100 ml), the combined organics washed with NaHCO$_3$ solution (100 ml), dried over sodium sulfate, and concentrated under vacuum. The residue was purified by chromatography on silica gel eluting with THF/chloroform (15:85→ 25:75), to give a white solid (1.25 g) after crystallization from THF/chloroform/MTBE: mp=169-171° C., LC-MS, MH$^+$=274; $^1$H NMR (300 MHz, CDCl$_3$) δ 7.94-7.88 (m, 2H); 7.54-7.47 (m, 1H); 4.83 (sb, 1H); 4.25 (sb, 1H); 4.09 (sb, 1H); 2.40-1.80 ppm (m, 8H).

EXAMPLE 6 exo-[2,1,3]-Benzoxadiazol-5-yl(3-hydroxy-8-azabicyclo[3.2.1]oct-8-yl)methanone

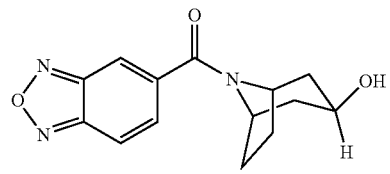 [SMILES: O=C(c1ccc2nonc2c1)N1C2CCC1CC(O)C2]

To a solution of endo-8-([2,1,3]-benzoxadiazol-5-ylcarbonyl)-8-azabicyclo[3.2.1]octan-3-ol (0.27 g, 0.98 mmol) in anhydrous THF (10 ml) were added 4-nitro benzoic acid (0.33 g, 2 mmol), triphenylphosphine (0.52 g, 2 mmol) and a solution of diisopropyl azodicarboxylate (0.4 g) in THF (1 ml). The mixture was stirred over night at room temperature, NaHCO$_3$ solution (50 ml) was added and the mixture extracted with ethyl acetate (2×100 ml). The organics were dried over sodium sulfate, concentrated under vacuum and the residue purified by chromatography on silica gel eluting with hexane/ethyl acetate (1:1), to give a white solid is (0.45 g). The preceding product was suspended in anhydrous methanol (70 ml), a solution of sodium (0.2 g) in anhydrous methanol (50 ml) was added and the mixture was stirred at room temperature for 0.75 h before adding conc. HCl (0.5 ml) (→ pH 3) and evaporating the solvent under vacuum. The crude product was purified by silica gel chromatography eluting with THF/chloroform (30:70), to give exo-[2,1,3]-benzoxadiazol-5-yl(3-hydroxy-8-azabicyclo[3.2.1]oct-8-yl)methanone as a white solid after crystallization from chloroform/MTBE (0.11 g): mp=176-177° C., LC-MS, MH$^+$=274; $^1$H NMR (300 MHz, CDCl$_3$) δ 7.94-7.90 (m, 2H); 7.21 (dd, 1H, J=9.3 and 1.2 Hz); 4.88 (sb, 1H); 4.30-4.10 (m, 2H); 4.09 (sb, 1H); 2.20-1.50 ppm (m, 8H).

EXAMPLE 7

2-Azabicyclo[2.2.1]hept-2-yl([2,1,3]-benzoxadiazol-5-yl)methanone

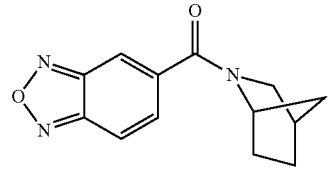 [SMILES: O=C(c1ccc2nonc2c1)N1CC2CCC1C2]

10% Pd/C (0.25 g) was added to a solution of 2-azabicyclo[2.2.1]hept-5-en-3-one in THF (30 ml) and dichloromethane (30 ml) and the mixture hydrogenated at room temperature for 18 h. The solids were filtered off, the solvent evaporated under vacuum, the residue dissolved in THF (60 ml) and lithium aluminum hydride (2 g) added slowly. The mixture was refluxed for 1 h and cooled to +5° C. before adding hexane (60 ml) and concentrated sodium hydroxide solution (4 ml). Celite (2 g) was added and the mixture stirred for 1 h before filtering off the solids and washing with THF (10 ml). To the mixture was added triethylamine (3 ml) and a solution of [2,1,3]-benzoxadiazole-5-carbonylchloride (2 g, 11.0 mmol) in dichloromethane (10 ml) and the mixture stirred overnight. Water (100 ml) was added, acidified to pH 2 with sulfuric acid and extracted with ethyl acetate (2×100 ml). The combined organics were washed with saturated sodium bicarbonate solution (100 ml), dried ($NaSO_4$) and evaporated onto silica gel (5 g) and the residue was chromatographed on silica gel eluting with ethyl acetate/hexane (1:1)→(3:1)→(1:0) to give the desired product as white crystals (0.28 g) after crystallization from MTBE/hexane: mp=92-93° C., LC-MS, $MH^+$=244; $^1$H NMR (300 MHz, $CDCl_3$, rotamers) δ 7.93-7.87 (m, 2H), 7.59-7.54 (m, 1H), 4.79 and 4.17 (s, total 1H), 3.61 and 3.48 (m, total 1H), 3.28 and 3.08 (dd, J=9.3 and 1.5 Hz, total 1H), 2.74 and 2.64 (s, total 1H), 1.90-1.47 ppm (m, 6H).

EXAMPLE 8

1-Azabicyclo[2.2.1]hept-1-yl([2,1,3]-benzoxadiazol-5-yl)methanone

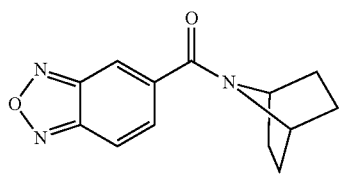 [SMILES: O=C(c1ccc2nonc2c1)N1C2CCC1CC2]

The title compound was prepared from 1-azabicyclo[2.2.1]heptane (*Org. Lett,* 2001, 3(9), 1371-1374) and [2,1,3]-benzoxadiazole-5-carbonylchloride as described for Example 7. The compound was isolated as a white crystalline solid: mp=143-144° C., LC-MS, $MH^+$=244; $^1$H NMR (300 MHz, $CDCl_3$) δ 8.00 (dd, J=1.2 and 1.2 Hz, 1H), 7.90 (dd, J=9.3 and 1.2 Hz, 1H), 7.59 (dd, J=1.2 and 9.3 Hz, 1H), 4.80 (br s, 1H), 4.16 (br s, 1H), 2.08-1.80 (m, 4H), 1.64-1.50 ppm (m, 4H).

EXAMPLE 9

2-Azabicyclo[2.2.2]oct-2-yl([2,1,3]-benzoxadiazol-5-yl)methanone

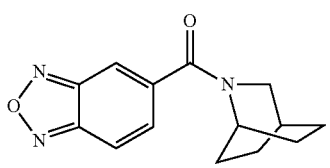 [SMILES: O=C(c1ccc2nonc2c1)N1CC2CCC1CC2]

Cis-4-Aminocyclohexanecarboxylic acid (2.0 g 13.96 mmol) was heated in a flask with a heat gun for 15 minutes. After cooling to room temperature, THF (70 ml) was added followed by lithium aluminum hydride (4 g), slowly and portion wise, and the mixture heated at 65° C. for 1 h. The mixture was cooled, and hexane (70 ml) and sodium hydroxide solution (5 ml) were added whilst rapidly stirring. Celite (5 g) was added and the mixture stirred overnight. The solids were removed by filtration and washed with THF (10 ml). Triethylamine (4 ml) was added followed by a solution of [2,1,3]-benzoxadiazole-5-carbonylchloride (2.0 g, 10.95 mmol) in dichloromethane (15 ml) and the mixture was stirred at room temperature for 0.3 h. Water (100 ml) was added, acidified to pH 2 with sulfuric acid and extracted with ethyl acetate (2×100 ml). The combined organics were washed with saturated sodium bicarbonate solution (100 ml), dried ($NaSO_4$) and evaporated under vacuum. The residue was chromatographed on silica gel eluting with ethyl acetate/dichloromethane/hexane (40:10:50) to give the desired product as a white solid (2.14 g): mp=138-139° C., LC-MS, $MH^+$=258; $^1$H NMR (300 MHz, $CDCl_3$, rotamers) δ 7.91 (dd, J=1.2 and 9.3 Hz, 1H), 7.90 and 7.83 (dd, J=1.2 and 1.2 Hz, total 1H), 7.51 and 7.46 (dd, J=1.2 and 9.3 Hz, total 1H), 4.58 and 3.42 (br s, total 1H), 3.68-2.64 (m, 2H), 2.12-1.61 ppm (m, 9H).

EXAMPLE 10

[2,1,3]-benzoxadiazol-5-yl(2-oxa-5azabicyclo[2.2.1]hept-5-yl)methanone

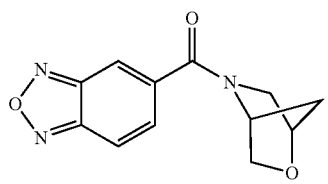 [SMILES: O=C(c1ccc2nonc2c1)N1CC2CC1CO2]

The title compound was prepared from 2-aza-5-oxabicyclo[2.2.1]heptane and [2,1,3]-benzoxadiazole-5-carbonylchloride as described for Example 7: mp=102-104° C., LC-MS, $MH^+$=246; $^1$H NMR (300 MHz, $CDCl_3$) δ 7.98-7.90 (m, 2H), 7.58 (dd, J=1.2 and 9.3 Hz, 1H), 5.08 and 4.78 (s, total 1H), 4.66 and 4.47 (s, total 1H), 4.05 (m, 1H), 3.89 (m, 1H), 3.73-3.63 (m, 1H), 3.52 (s, 1H), 2.06-1.95 ppm (m, 2H).

EXAMPLE 11

2-Azabicyclo[2.2.1]hept-5-en-2-yl([2,1,3]-benzoxadiazol-5-yl)methanone

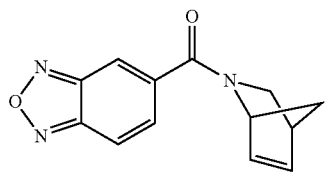 [SMILES: O=C(c1ccc2nonc2c1)N1CC2C=CC1C2]

Prepared from 2-azabicyclo[2.2.1]hept-5-en-3-one by reducing with $LiAlH_4$ and then coupling the resultant 2-azabicyclo[2.2.1]hept-5-ene with [2,1,3]-benzoxadiazole-5-carbonylchloride as described for Example 7. The title product was isolated as a white solid after crystallization from MTBE/hexane: mp=106-108° C., LC-MS, MH$^+$=242.25; $^1$H NMR (300 MHz, CDCl$_3$, rotamers) δ 7.98-7.86 (m, 2H), 7.58-7.53 (m, 1H), 6.60-6.50 (m, 1H), 6.36-6.32 (m, 1H), 5.25 and 4.57 (s, total 1H), 3.67-3.62 (m, 1H), 3.39 and 3.32 (s, total 1H), 3.03 and 2.70 (both d, J=10.2 and 8.7 Hz respectively, total 1H), 1.75 ppm (s, 2H).

EXAMPLE 12 and EXAMPLE 13

R-2-Azabicyclo[2.2.1]hept-5-en-2-yl([2,1,3]-benzoxadiazol-5-yl)methanone and S-2-Azabicyclo[2.2.1]hept-5-en-2-yl([2,1,3]-benzoxadiazol-5-yl)methanone

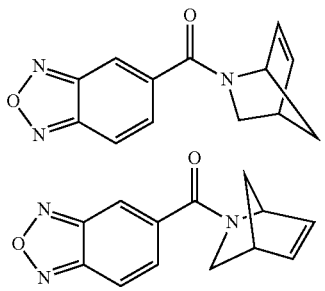

The title compounds were prepared from (R)-2-azabicyclo[2.2.1]hept-5-en-3-one and (S)-2-azabicyclo[2.2.1]hept-5-en-3-one using the procedures described for Example 11. R-2-Azabicyclo[2.2.1]hept-5-en-2-yl([2,1,3]-benzoxadiazol-5-yl)methanone: mp=104-106° C. S-2-Azabicyclo[2.2.1]hept-5-en-2-yl([2,1,3]-benzoxadiazol-5-yl)methanone: mp=104-106° C.

EXAMPLE 14

[2,1,3]-Benzoxadiazol-5-yl(5,6-dichloro-2-azabicyclo[2.2.1]hept-2-yl)methanone

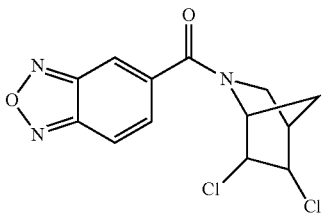 [SMILES: O=C(c1ccc2nonc2c1)N1CC2CC1C(Cl)C2Cl]

Concentrated HCl (3 ml) was added to a rapidly stirred mixture of bleach (20 ml) in dichloromethane at room temperature. The mixture was added to a stirred solution of 2-azabicyclo[2.2.1]hept-5-en-2-yl([2,1,3]-benzoxadiazol-5-yl) (0.5 g, 2.07 mmol) in dichloromethane (50 ml). The mixture was evaporated and the residue purified by chromatography on silica gel eluting with ethyl acetate/hexane (2:3) to give the title compound as a white solid after crystallization from dichloromethane/MTBE: mp=156-157° C., LC-MS, MH$^+$=312.16; $^1$H NMR (300 MHz, CDCl$_3$, rotamers) δ 8.02-7.95 (m, 2H), 7.52 (dd, J=1.1 and 9.2 Hz, 1H), 4.89 and 4.29 (s, total 1H), 4.24-4.15 (m, 2H), 3.72-2.40 4.57 ppm (m, 5H).

II. Biological Methods

EXAMPLE 15

In Vivo Electrophysiology

The electrophysiological effects of invention compounds were tested in vivo in anesthetized animals according to the following procedures.

Animals are maintained under anesthesia by phenobarbital administered using a Hamilton syringe pump. Stimulating and recording electrodes are inserted into the perforant path and dentate gyrus of the hippocampus, respectively. Once electrodes are implanted, a stable baseline of evoked responses are elicited using single monophasic pulses (100 μs pulse duration) delivered at 3/min to the stimulating electrode. Field EPSPs are monitored until a stable baseline is achieved (about 20-30 min), after which a solution of test compound is injected intraperitoneally and evoked field potentials are recorded. Evoked potentials are recorded for approximately 2 h following drug administration or until the amplitude of the field EPSP returns to baseline. In the latter instance, it is common that an iv administration is also carried out with an appropriate dose of the same test compound.

EXAMPLE 2

Inhibition of d-Amphetamine Stimulated Locomotion

Male CD1 mice, 25-30 gm body weight, were brought into the experimental room and allowed at least 30 min of acclimation. Each mouse was placed into the testing enclosure with an infrared beam array that automatically monitors the animal's activity. Mice were habituated in the testing enclosure for 20 min, and then returned to their home cage. Mice were dosed intraperitoneally with test compound in appropriate vehicle 5 minutes before d-Amphetamine injection. Ten minutes after d-Amphetamine injection, mice were tested for locomotor activity for a total of 15 minutes. The data was computer collected and expressed as "arbitrary movement units." All data were analyzed by comparing the groups treated with the test compound to the vehicle control group. Statistical analysis was performed by ANOVA followed by Dunnet's t-test where P less than 0.05 were considered to be significantly different.

While the invention has been described with reference to specific methods and embodiments, it will be appreciated that various modifications may be made without departing from the invention.

What is claimed:
1. A compound according to formula A:

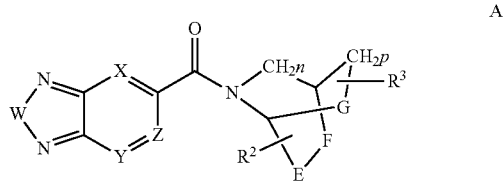

wherein:

W is oxygen;

X, Y and Z are independently selected from the group consisting of —N, or —CR, wherein:

R is H, —Br, —Cl, —F, —CN, —NO$_2$, —OR$^1$, —SR$^1$, —NR$^1_2$, —C$_1$-C$_6$ branched or un-branched alkyl, which may be un-substituted or substituted, wherein:

R$^1$ is H, —C$_1$-C$_6$ branched or un-branched alkyl which, may be un-substituted or substituted, n is 0, 1, 2, 3, 4, 5 m is 0, 1, 2, 3, 4, 5 p is 0, 1, 2, 3, 4, 5

R$^2$ and R$^3$ are each independently selected from H, a halogen, —CN, —NO$_2$, —OR$^1$, —SR$^1$, —NR$^1_2$, CF$_3$, OH, C=O, a —C$_1$-C$_6$ branched or un-branched alkyl, which may be un-substituted or substituted, a —C$_2$-C$_6$ branched or un-branched alkenyl, which may be un-substituted or substituted, a —C$_2$-C$_6$ branched or un-branched alkynyl, which may be un-substituted or substituted, a —C$_3$-C$_7$ cycloalkyl which may be un-substituted or substituted, an aryl which may be un-substituted or substituted, a heterocycle which may be un-substituted or substituted, a carboxyalkyl which may be un-substituted or substituted, a carboxyaryl which may be unsubstituted or substituted, a carboxy-heteroaryl which may be un-substituted or substituted, a sulfonylalkyl which may be un-substituted or substituted, a sulfonylaryl which may be unsubstituted or substituted or a sulfonylheteroaryl which may be un-substituted or substituted, E and F are each independently selected from CH$_2$m, CR$^2$R$^3$, A, CH$_2$A, CR$^2$=CR$^3$ or are absent, with the proviso that E and F are not both absent;

G is CR$^2$R$^3$, A, CH$_2$A, CR$^2$=CR$^3$, CH$_2$C=O, CH$_2$CR$^2$R$^3$, or absent, A is O, S, SO, SO$_2$, C=O or CR$^2$R$^3$;

or a pharmaceutically acceptable salt, solvate, or polymorph thereof.

2. The compound according to claim 1 compound according to the formula:

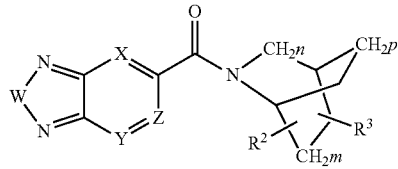

I wherein:

W is oxygen;

X, Y and Z are independently selected from the group consisting of —N, or —CR, wherein:

R is H, —Br, —Cl, —F, —CN, —NO$_2$, —OR$^1$, —SR$^1$, —NR$^1_2$, —C$_1$-C$_6$ branched or un-branched alkyl, which may be un-substituted or substituted, wherein:

R$^1$ is H, —C$_1$-C$_6$ branched or un-branched alkyl which, may be un-substituted or substituted, n is 0-5 m is 0-5 p is 0-5

R$^2$ and R$^3$ are independently selected from H, a halogen, —CN, —NO$_2$, —OR$^1$, —SR$^1$, —NR$^1_2$, CF$_3$, OH, C=O, a —C$_1$-C$_6$ branched or un-branched alkyl, which may be un-substituted or substituted, a —C$_2$-C$_6$ branched or un-branched alkenyl, which may be un-substituted or substituted, a —C$_2$-C$_6$ branched or un-branched alkynyl, which may be un-substituted or substituted, a —C$_3$-C$_7$ cycloalkyl which may be un-substituted or substituted, an aryl which may be un-substituted or substituted, a heterocycle which may be un-substituted or substituted, a carboxyalkyl which may be un-substituted or substituted, a carboxyaryl which may be un-substituted or substituted, a carboxy-heteroaryl which may be un-substituted or substituted, a sulfonylalkyl which may be unsubstituted or substituted, a sulfonylaryl which may be un-substituted or substituted or a sulfonylheteroaryl which may be un-substituted or substituted, or a pharmaceutically acceptable salt, solvate, or polymorph thereof.

3. A compound according to claim 1 according to the formula:

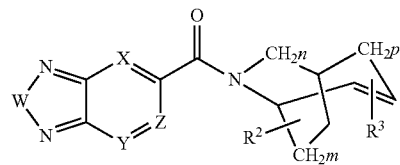

II wherein:

W, X, Y and Z are as defined for structure I of claim 1 n is 0-5 m is 0-5 p is 0-4 and R$^2$ and R$^3$ are as defined for structure I of claim 1, or a pharmaceutically acceptable salt, solvate, or polymorph thereof.

4. A compound according to claim 1 of the formula:

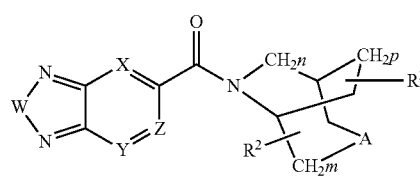

III wherein:

W, X, Y and Z are as defined for structure I

A is O, S, SO, SO$_2$, C=O or CR$^2$R$^3$;

n is 0-5 m is 1-5 p is 0-5 and R$^2$ and R$^3$ are as defined for structure I, or a pharmaceutically acceptable salt, solvate, or polymorph thereof.

5. A compound according to claim 1 of the formula:

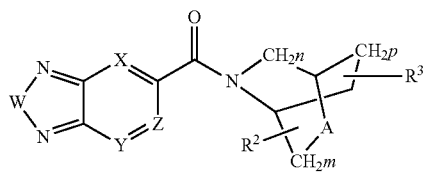

wherein:
W, X, Y and Z are as defined for structure I
A is O, S, SO, SO$_2$, C=O or CR$^2$R$^3$;
n =1-5
m =1-5
p =0-5
and R$^2$ and R$^3$ are as defined for structure I, or a pharmaceutically acceptable salt, solvate, or polymorph thereof.

6. A compound according to Formula I of claim 2 which is:
8-Azabicyclo[3.2.1]oct-8-yl([2,1,3]-benzoxadiazol-5-yl)methanone,
[2,1,3]-Benzoxadiazol-5-yl(3,3-difluoro-8-azabicyclo[3.2.1]oct-8-yl)methanone,
endo-[2,1,3]-Benzoxadiazol-5-yl(3-hydroxy-8-azabicyclo[3.2.1]oct-8-yl)methanone,
exo-[2,1,3]-Benzoxadiazol-5-yl(3-hydroxy-8-azabicyclo[3.2.1]oct-8-yl)methanone,
2-Azabicyclo[2.2.1]hept-2-yl([2,1,3-benzoxadiazol-5-yl)methanone,
1-Azabicyclo[2.2.1]hept-1-yl([2,1,3]-benzoxadiazol-5-yl)methanone,
2-Azabicyclo[2.2.2]oct-2-yl([2,1,3]-benzoxadiazol-5-yl)methanone or
[2,1,3]-Benzoxadiazol-5-yl(5,6-dichloro-2-azabicyclo[2.2.1]hept-2-yl)methanone.

7. A compound according to Formula II of claim 3 which is:
[2,1,3]-Benzoxadiazol-5-yl(3-fluoro-8-azabicyclo[3.2.1]oct-2-en-8-yl)methanone,
R-2-Azabicyclo[2.2.1]hept-5-en-2-yl([2,1,3]-benzoxadiazol-5-yl)methanone or
S-2-Azabicyclo[2.2.1]hept-5-en-2-yl([2,1,3]-benzoxadiazol-5-yl)methanone.

8. A compound according to claim 1 which is:
[2,1,3]-Benzoxadiazol-5-yl(2-oxa-5azabicyclo [2.2.1]hept-5-yl)methanone,
8-([2,1,3 ]-Benzoxadiazol-5-ylcarbonyl)-8-azabicyclo[3.2.1 ]octan-3 -one, or
2-Azabicyclo [2.2.1 ]hept-5 -en-2-yl([2,1,3]-benzoxadiazol-5-yl)methanone.

9. A method for the treatment of impairment of memory or other cognitive function in a mammalian subject in need, wherein the subject suffers from a hypoglutamatergic condition or a deficiency in the number or strength of excitatory synapses or in the number of AMPA receptors, said method comprising administering to said subject, in a pharmaceutically acceptable carrier, an effective amount of a compound according to claim 1.

10. A method for the treatment of schizophrenia or schizophreniform behavior in a mammalian subject in need, wherein the subject suffers from a hypoglutamatergic condition or deficiencies in the number or strength of excitatory synapses or in the number of AMPA receptors such that a cortical/striatal imbalance occurs, said method comprising administering to said subject, in a pharmaceutically acceptable carrier, an effective amount of a compound according to claim 1.

11. The method according to claim 10 wherein said subject is treated for schizophrenia.

12. A method of treating Parkinson's disease in a patient in need thereof, said method comprising administering to said patient an effective amount of a compound according to claim 1.

13. A method of treating ADHD in a patient in need thereof, said method comprising administering to said patient an effective amount of a compound according to claim 1.

14. A method of treating Rett Syndrome in a patient in need thereof, said method comprising administering to said patient an effective amount of a compound according to claim 1.

15. A method of treating Fragile-X Syndrome in a patient in need thereof, said method comprising administering to said patient an effective amount of a compound according to claim 1.

16. A method of treating breathing related sleep disorders or sleep apnea in a patient in need thereof, said method comprising administering to said patient an effective amount of a compound according to claim 1.

17. A method of treating Alzheimer's disease in a patient in need thereof, said method comprising administering to said patient an effective amount of a compound according to claim 1.

18. A method of treating Alzheimer's disease in a patient in need thereof, said method comprising administering to said patient an effective amount of a compound according to claim 1 in combination with at least one acetylcholinesterase inhibitor.

* * * * *